US010695166B2

(12) United States Patent
Willis et al.

(10) Patent No.: US 10,695,166 B2
(45) Date of Patent: Jun. 30, 2020

(54) INTRAOCULAR LENSES (IOLS) AND RELATED ASSEMBLIES AND INTRAOCULAR ATTACHMENT METHODS

(71) Applicant: Timothy R. Willis, Raleigh, NC (US)

(72) Inventors: Timothy R. Willis, Raleigh, NC (US); Steven Bacich, Half Moon Bay, CA (US)

(73) Assignee: Timothy R. Willis, Raleigh, NC (US)

( * ) Notice: Subject to any disclaimer, the term of this patent is extended or adjusted under 35 U.S.C. 154(b) by 0 days.

(21) Appl. No.: 15/752,409

(22) PCT Filed: Aug. 15, 2016

(86) PCT No.: PCT/US2016/046990
§ 371 (c)(1),
(2) Date: Feb. 13, 2018

(87) PCT Pub. No.: WO2017/031037
PCT Pub. Date: Feb. 23, 2017

(65) Prior Publication Data
US 2019/0000610 A1    Jan. 3, 2019

Related U.S. Application Data

(60) Provisional application No. 62/205,226, filed on Aug. 14, 2015.

(51) Int. Cl.
*A61F 2/16* (2006.01)
*A61F 9/007* (2006.01)

(52) U.S. Cl.
CPC .......... *A61F 2/1608* (2015.04); *A61F 2/1613* (2013.01); *A61F 2/1664* (2013.01);
(Continued)

(58) Field of Classification Search
CPC .................................................. A61F 2/1608
See application file for complete search history.

(56) References Cited

U.S. PATENT DOCUMENTS 3,922,728 A    12/1975    Krasnov
3,991,426 A    11/1976    Flom et al.
(Continued)

FOREIGN PATENT DOCUMENTS

EP    0691109 A1    1/1996
JP    H10506026 A    6/1998
(Continued)

OTHER PUBLICATIONS

European Search Report for European Patent Application No. 16837636.6, dated Sep. 5, 2018, 5 pages.
(Continued)

*Primary Examiner* — Leslie Lopez
(74) *Attorney, Agent, or Firm* — Withrow & Terranova, PLLC

(57) ABSTRACT

Intraocular lenses and related assemblies and intraocular attachment methods are disclosed herein. In one embodiment, an intraocular lens assembly comprises a helical-shaped coil fastener to affix an intraocular lens to an iris to correct for astigmatism, presbyopia, and/or myopia or hyperopia. The helical-shaped coil fastener comprises a head and a helical wire extending from a bottom surface of the head and comprising a pointed tip opposite the head. The helical-shaped coil fastener is configured to be affixed to the iris by rotatable penetration of the iris, and thus can be removed from the iris by reverse rotation of the helical-shaped coil fastener. The helical-shaped coil fastener has a low volume, large surface area, low cross-sectional area of penetration, and an oblique angle of penetration. Thus, the helical-shaped coil fastener is easy to apply, easy to remove, (Continued)

minimizes tissue damage, maximizes stability, and minimizes penetration force.

20 Claims, 21 Drawing Sheets

(52) U.S. Cl.
CPC ...... *A61F 9/007* (2013.01); *A61F 2002/1681* (2013.01); *A61F 2220/0008* (2013.01)

(56) References Cited

U.S. PATENT DOCUMENTS

| | | | |
|---|---|---|---|
| 3,996,626 A | 12/1976 | Richards et al. | |
| 4,053,953 A | 10/1977 | Flom et al. | |
| 4,126,904 A | 11/1978 | Shepard | |
| 4,166,293 A | 9/1979 | Otnis | |
| 4,177,526 A | 12/1979 | Kuppinger et al. | |
| 4,206,518 A | 6/1980 | Jardon et al. | |
| 4,215,440 A | 8/1980 | Worst | |
| 4,304,012 A | 12/1981 | Richard | |
| 4,343,050 A | 8/1982 | Kelman | |
| 4,440,169 A | 4/1984 | Schulman | |
| 4,535,488 A | 8/1985 | Haddad | |
| 4,536,895 A | 8/1985 | Bittner | |
| 4,542,540 A | 9/1985 | White | |
| 4,575,374 A | 3/1986 | Anis | |
| 4,589,147 A | 5/1986 | Nevyas | |
| 4,676,792 A | 6/1987 | Praeger | |
| 4,676,794 A | 6/1987 | Kelman | |
| 4,706,666 A | 11/1987 | Sheets | |
| 4,863,462 A | 9/1989 | Fedorov et al. | |
| 4,898,461 A | 2/1990 | Portney | |
| 4,950,288 A | 8/1990 | Kelman | |
| 5,047,052 A | 9/1991 | Dubroff | |
| 5,098,444 A | 3/1992 | Feaster | |
| 5,135,530 A | 8/1992 | Lehmer | |
| 5,152,299 A | 10/1992 | Soukup | |
| 5,192,319 A | 3/1993 | Worst | |
| 5,217,491 A | 6/1993 | Vanderbilt | |
| 5,222,960 A | 6/1993 | Poley | |
| 5,258,025 A | 11/1993 | Fedorov et al. | |
| 5,364,405 A | 11/1994 | Zaleski | |
| 5,366,501 A | 11/1994 | Langerman | |
| 5,395,378 A | 3/1995 | McDonald | |
| 5,476,514 A | 12/1995 | Cumming | |
| 5,480,428 A | 1/1996 | Fedorov et al. | |
| 5,494,484 A | 2/1996 | Feingold | |
| 5,618,307 A | 4/1997 | Donlon et al. | |
| 5,628,796 A | 5/1997 | Suzuki | |
| 5,657,108 A | 8/1997 | Portney | |
| 5,658,327 A | 8/1997 | Altman et al. | |
| 5,690,641 A | 11/1997 | Sorensen et al. | |
| 5,720,742 A | 2/1998 | Zacharias | |
| 5,877,839 A | 3/1999 | Portney | |
| 5,928,282 A | 7/1999 | Nigam | |
| 5,942,277 A | 8/1999 | Makker et al. | |
| 5,968,094 A | 10/1999 | Werblin et al. | |
| 6,051,024 A | 4/2000 | Cumming | |
| 6,096,077 A | 8/2000 | Callahan et al. | |
| 6,152,958 A | 11/2000 | Nordan | |
| 6,152,959 A | 11/2000 | Portney | |
| 6,186,625 B1 | 2/2001 | Portney | |
| 6,197,058 B1 | 3/2001 | Portney | |
| 6,197,059 B1 | 3/2001 | Cumming | |
| 6,200,342 B1 | 3/2001 | Tassignon | |
| 6,228,115 B1 | 5/2001 | Hoffmann et al. | |
| 6,231,603 B1 | 5/2001 | Lang et al. | |
| 6,241,777 B1 | 6/2001 | Kellan | |
| 6,261,321 B1 | 7/2001 | Kellan | |
| 6,342,058 B1 | 1/2002 | Portney | |
| 6,342,073 B1 | 1/2002 | Cumming et al. | |
| 6,395,028 B1 | 5/2002 | Tran et al. | |
| 6,398,809 B1 | 6/2002 | Hoffmann et al. | |
| 6,478,821 B1 | 11/2002 | Laguette et al. | |
| 6,503,276 B2 | 1/2003 | Lang et al. | |
| 6,527,389 B2 | 3/2003 | Portney | |
| 6,537,281 B1 | 3/2003 | Portney | |
| 6,554,860 B2 | 4/2003 | Hoffmann et al. | |
| 6,585,768 B2 | 7/2003 | Hamano et al. | |
| 6,699,284 B2 | 3/2004 | Sunada | |
| 6,770,093 B2 | 8/2004 | Worst et al. | |
| 6,814,439 B2 | 11/2004 | Portney | |
| 6,827,738 B2 | 12/2004 | Willis et al. | |
| 6,918,930 B2 | 7/2005 | Portney | |
| 6,991,651 B2 | 1/2006 | Portney | |
| 7,008,449 B2 | 3/2006 | Willis et al. | |
| 7,128,754 B2 | 10/2006 | Bolduc | |
| 7,806,917 B2 | 10/2010 | Xiao | |
| 8,231,639 B2 | 7/2012 | Bolduc et al. | |
| 8,486,140 B2 | 7/2013 | Willis et al. | |
| 8,551,164 B2 | 10/2013 | Willis et al. | |
| 2001/0044657 A1 | 11/2001 | Kellan | |
| 2002/0029048 A1 | 3/2002 | Miller | |
| 2002/0193877 A1 | 12/2002 | Hoffman et al. | |
| 2003/0195622 A1 | 10/2003 | Hoffmann et al. | |
| 2004/0006387 A1 | 1/2004 | Kelman | |
| 2004/0015235 A1 | 1/2004 | Worst et al. | |
| 2004/0156013 A1 | 8/2004 | Lindacher et al. | |
| 2004/0204703 A1 | 10/2004 | Rozakis et al. | |
| 2004/0207807 A1 | 10/2004 | Lindacher | |
| 2004/0225357 A1 | 11/2004 | Worst et al. | |
| 2005/0015143 A1* | 1/2005 | Willis .................. A61F 2/1608 623/6.36 |
| 2005/0019371 A1* | 1/2005 | Anderson ............ A61K 9/0051 424/426 |
| 2005/0246016 A1 | 11/2005 | Miller et al. | |
| 2005/0288683 A1 | 12/2005 | Worst et al. | |
| 2006/0004445 A1 | 1/2006 | Frans Worst et al. | |
| 2006/0095127 A1 | 5/2006 | Feingold et al. | |
| 2006/0116760 A1 | 6/2006 | Thornton et al. | |
| 2006/0142856 A1 | 6/2006 | Willis et al. | |
| 2007/0027452 A1 | 2/2007 | Varner et al. | |
| 2007/0142911 A1 | 6/2007 | Willis et al. | |
| 2007/0142912 A1 | 6/2007 | Willis et al. | |
| 2007/0239158 A1* | 10/2007 | Trieu ................. A61B 17/7059 606/279 |
| 2008/0086154 A1 | 4/2008 | Taylor et al. | |
| 2008/0097523 A1* | 4/2008 | Bolduc ............... A61B 17/064 606/219 |
| 2008/0109077 A1 | 5/2008 | Bos | |
| 2009/0082861 A1 | 3/2009 | Marunaka et al. | |
| 2010/0010514 A1 | 1/2010 | Ishioka et al. | |
| 2010/0152848 A1 | 6/2010 | Williamson et al. | |
| 2011/0029075 A1 | 2/2011 | Willis et al. | |
| 2012/0179163 A1* | 7/2012 | Housman .......... A61B 17/0401 606/104 |

FOREIGN PATENT DOCUMENTS

| | | |
|---|---|---|
| JP | 2002360616 A | 12/2002 |
| WO | 9220302 A1 | 11/1992 |
| WO | 9962434 A1 | 12/1999 |
| WO | 0061036 A1 | 10/2000 |
| WO | 0187182 A2 | 11/2001 |
| WO | 0187188 A2 | 11/2001 |
| WO | 0217818 A1 | 3/2002 |
| WO | 0247584 A1 | 6/2002 |
| WO | 03009051 A2 | 1/2003 |
| WO | 2004092805 A1 | 10/2004 |
| WO | 2007121080 A2 | 10/2007 |

OTHER PUBLICATIONS

"Phakic IOL's Getting Closer to Market," Ocular Surgery News, Sep. 1, 2000, 5 pages.
"Artisan Myopia & Hyperopia 'Doing Well' in Phase 3 Trials," Ocular Surgery News, Sep. 1, 2000, 3 pages.
Bron, Anthony J., et al., "Wolff's Anatomy of the Eye and Orbit," Eighth edition, Sep. 4, 1998, pp. 22, 223, and 308-334.
"Refractive Surgery: In European Experience, Phakic IOLs A Story of Hope and Disappointment," Available online at: <<http://www.osnsupersite.com/printasp?rID=28260>>, May 14, 2008, 2 pages.

(56) References Cited

OTHER PUBLICATIONS

International Search Report and Written Opinion for PCT/US2016/46990, dated Oct. 28, 2016, 13 pages.
International Preliminary Report on Patentability for PCT/US2016/46990, dated Dec. 7, 2017, 34 pages.
The First Office Action for Chinese Patent Application No. 201680055450.8, dated Jan. 24, 2019, 15 pages.
Decision of Rejection for Japanese Patent Application No. 2018-507685, dated Dec. 25, 2018, 3 pages.
Notice of Reasons for Rejection for Japanese Patent Application No. 2018-507685, dated Jul. 3, 2018, 6 pages.
Examination Report for European Patent Application No. 16837636.6, dated Oct. 1, 2018, 5 pages.
Decision to Grant a Patent for Japanese Patent Application No. 2018-507685, dated Apr. 9, 2019, 4 pages.
The Second Office Action for Chinese Patent Application No. 201680055450.8, dated Oct. 10, 2019, 26 pages.

\* cited by examiner

INTRAOCULAR LENSES (IOLS) AND RELATED ASSEMBLIES AND INTRAOCULAR ATTACHMENT METHODS

STATEMENT OF RELATED APPLICATIONS

The present application claims the benefit of priority under 35 U.S.C. § 371 of International Patent Application No. PCT/US2016/046990, filed on Aug. 15, 2016, entitled "Intraocular Lenses (IOLs) and Related Assemblies and Intraocular Attachment Methods," which in turn claims the benefit of priority under 35 U.S.C. § 119(e) of U.S. Provisional Patent Application Ser. No. 62/205,226 filed on Aug. 14, 2015, entitled "Apparatus and Methods for Refractive Intraocular Implant System," the contents of which are relied upon and incorporated by reference herein in their entireties.

FIELD OF THE DISCLOSURE

The field of the disclosure relates generally to apparatuses and methods for intraocular attachment systems, and more particularly to implant design, surgical methods, tools, and fasteners for affixing an intraocular implant to an iris.

BACKGROUND

Patients and surgeons have long been interested in alternatives to eyeglasses to compensate for eye abnormalities. These alternatives include for example contact lenses, radial keratotomy, LASIK or laser vision correction surgery, etc. However, such alternatives are not without their drawbacks and deficiencies. For example, LASIK surgery has correction power limitations, can cause weakening of a patient's cornea, and can induce other complications (e.g., vision fluctuation, halos, glare, dry eye, etc.).

Accordingly, intraocular lenses (IOLs) that can be implanted into the eye have become an increasingly popular alternative for providing correction, particularly for patients for whom LASIK surgery is not an option. An IOL is a lens surgically implanted within the eye and usually comprises a lens and one or more haptics, which serve to affix the lens to the eye and hold the lens in place. There are a couple of different types of intraocular lenses including phakic intraocular lenses and aphakic intraocular lenses. IOLs are usually surgically positioned within the anterior chamber of the eye or between the iris and crystalline lens, and many are affixed in the angle of the eye or the anterior surface of the iris. An IOL can be placed over, and work with, an existing natural lens of an eye to modify the eye's optical power and performance, and in particular to correct for errors in the eye's focusing power, such as presbyopic refraction error and/or myopic or hyperopia refraction error.

However, some IOLs require multiple incisions, large incisions, and/or a multi-handed simultaneous ambidextrous surgical technique (e.g., two-handed, three-handed or requiring multiple instrument passes from hand-to-hand) to insert and attach to an iris or require special sizing (e.g., implants placed between the human crystalline lens and iris) not know until the time or surgery. Further, the means used to affix the IOL within the eye is typically designed to ensure fixation and prevent unintentional detachment, and as a result, the fixation means may inflict significant tissue damage to the iris and/or be difficult to remove. This may contribute to surgical or clinical failures of some IOLs, which could include lens insertion and attachment problems, intraocular or iris bleeding, inflammation, endothelial cell loss, pupil deformation, or lens induced glaucoma. Thus, many of the current IOLs are surgically difficult to insert and affix, require large incisions within the cornea for surgical access, are difficult to remove, and/or lead to complications as a result of iris tissue aggravation and damage and/or corneal endothelial cell loss.

SUMMARY OF THE DETAILED DESCRIPTION

Embodiments disclosed herein include intraocular lenses (IOLs) and related assemblies and implant and intraocular attachment methods. In some aspects, a helical-shaped coil fastener is provided, and associated applicator tool and surgical insertion methods, to affix an IOL to an iris relative to a pupil. In one embodiment, an IOL assembly comprises a helical-shaped coil fastener to affix an IOL to an iris to correct for astigmatism, presbyopia, and/or myopia or hyperopia. The IOL can be implanted with the patient's natural crystalline lens removed or left in place to correct for errors in vision. The IOL could be used as a phakic implant (e.g., for use with the crystalline lens) or as an aphakic implant (e.g., for use without the crystalline lens). The IOL has an optic with an optical effect (e.g., a first optical effect) to correct for astigmatism and/or myopia or hyperopia. The IOL may also have another optical effect (e.g., a second optical effect) to address presbyopia (e.g., as a phakic IOL working in combination with crystalline lens at up to 2.0 diopter) or as an aphakic IOL to address presbyopia (e.g., up to 4.0 diopter). The optic also has one or more haptics extending from a peripheral edge thereof configured to facilitate affixation of the IOL to the iris relative to the pupil. The haptic can be vaulted to minimize iris issue contact while maintaining an appropriate distance from the cornea. In this regard, a helical-shaped coil fastener is provided that is configured to engage the optic to affix the IOL to the iris. The helical-shaped coil fastener comprises a head and a helical wire extending from a bottom surface of the head and comprising a pointed tip opposite the head. Once the IOL is positioned relative to the pupil, the helical-shaped coil fastener is configured to be applied to a distal end of each haptic to penetrate the anterior surface of the iris at an oblique angle, thereby affixing the IOL relative to the pupil. The helical-shaped coil fastener is configured to be affixed to the iris by rotatable penetration of the iris, and thus can be removed from the iris by reverse rotation of the helical-shaped coil fastener. The helical-shaped coil fastener has a low volume, large surface area, low cross-sectional area of penetration, and an oblique angle of penetration. Thus, the helical-shaped coil fastener is easy to apply, easy to remove, minimizes tissue damage, maximizes stability, and minimizes penetration force.

Additional embodiments disclosed herein are directed to other fasteners, IOLs, IOL assemblies, and methods to affix an IOL to an iris to correct for astigmatism, presbyopia, and/or myopia or hyperopia. In this regard, some additional embodiments provide fasteners configured to engage an optic of an IOL to affix the IOL to the iris. These additional embodiments could also have one or more features to facilitate and/or control fastener penetration placement and/or penetration depth in affixing an IOL to an iris.

In this regard in one embodiment, an intraocular lens assembly configured to be inserted and affixed in an eye with a crystalline lens comprises an intraocular lens, a haptic, and a helical-shaped coil fastener. The intraocular lens comprises an optic for producing a preselected optical effect, the optic comprising an outer peripheral edge. The haptic extends from the outer peripheral edge of the optic and comprises a proximal end, a distal end, and a riser section therebetween. The proximal end of the haptic is at the outer peripheral edge of the optic at a different height than the distal end. The helical-shaped coil fastener comprises a wire comprising an end portion with a pointed tip. The helical-shaped coil fastener is configured to affix the haptic to the eye by insertion through the distal end of the haptic and rotatable penetration into an anterior side of an iris to compress a portion of the haptic between a top portion of the helical-shaped coil fastener and the anterior side of the iris.

In another embodiment, a surgical method for treating an eye condition with an intraocular lens assembly comprises creating an incision in an eye to be treated, and inserting a folded intraocular lens and haptic through the incision into the eye. The folded intraocular lens unfolds after insertion into the eye. The intraocular lens comprises an optic for producing a preselected optical effect. The haptic extends from an outer peripheral edge of the optic. The surgical method further comprises affixing the intraocular lens to an anterior side of an iris of the eye by inserting a helical-shaped coil fastener through a distal end of the haptic and rotatably penetrating the helical-shaped coil fastener into the iris to compress a portion of the haptic between a top portion of the helical-shaped coil fastener and an anterior side of the iris. The helical-shaped coil fastener comprises a wire comprising an end portion with a pointed tip.

In another embodiment, a surgical tool for affixing an intraocular lens to an iris comprises a handle, a cannula, and a driver. The handle with an actuator control accessible to a user. The cannula extends from an end of the handle and comprises a proximal opening and a distal opening. The distal opening is able to be oriented at a non-linear angle relative to the proximal opening. The cannula is configured to allow rotation and translation of a helical-shaped coil fastener therein. The driver is configured to translate the helical-shaped coil fastener from an interior of the cannula through the distal opening of the cannula responsive to the actuator control. The surgical tool is configured to rotate the helical-shaped coil fastener as the helical-shaped coil fastener exits through the distal opening of the cannula.

DETAILED DESCRIPTION

Figure 1A:
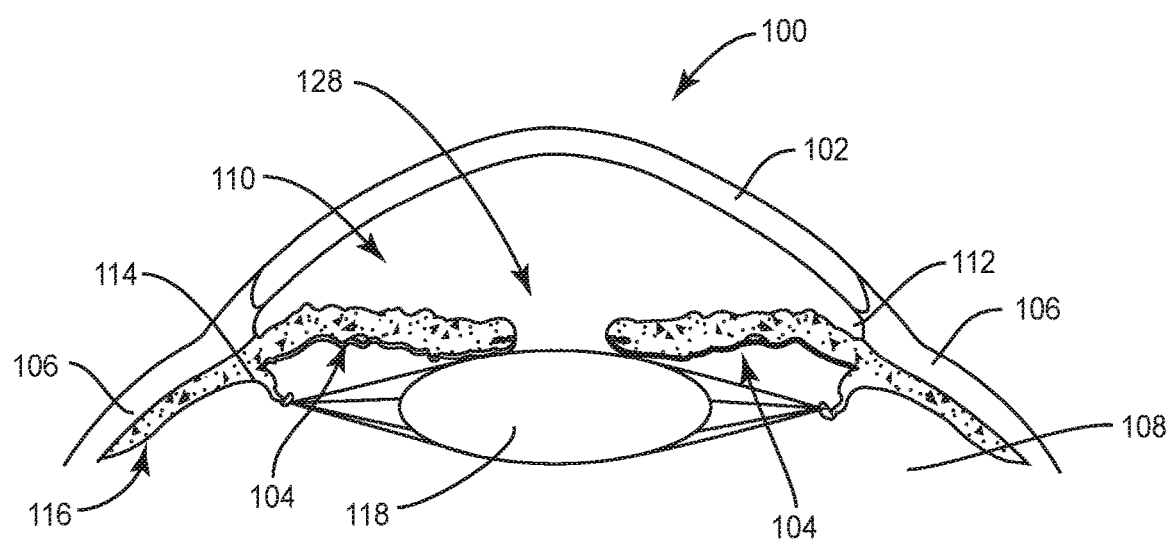
FIG. 1A is a cross-sectional view of a human eye.

Embodiments disclosed herein include intraocular lenses (IOLs) and related assemblies and implant and intraocular attachment methods. In some aspects, a helical-shaped coil fastener is provided, and associated applicator tool and surgical insertion methods, to affix an IOL to an iris relative to a pupil. In one embodiment, an IOL assembly comprises a helical-shaped coil fastener to affix an IOL to an iris to correct for astigmatism, presbyopia, and/or myopia or hyperopia. The IOL can be implanted with the patient's natural crystalline lens removed or left in place to correct for errors in vision. The IOL could be used as a phakic implant (e.g., for use with the crystalline lens) or as an aphakic implant (e.g., for use without the crystalline lens). The IOL has an optic with an optical effect (e.g., a first optical effect) to correct for astigmatism and/or myopia or hyperopia. The IOL may also have another optical effect (e.g., a second optical effect) to address presbyopia (e.g., as a phakic IOL working in combination with crystalline lens at up to 2.0 diopter) or as an aphakic IOL to address presbyopia (e.g., up to 4.0 diopter). The optic also has one or more haptics extending from a peripheral edge thereof configured to facilitate affixation of the IOL to the iris relative to the pupil. The haptic can be vaulted to minimize iris issue contact while maintaining an appropriate distance from the cornea. In this regard, a helical-shaped coil fastener is provided that is configured to engage the optic to affix the IOL to the iris. The helical-shaped coil fastener comprises a head and a helical wire extending from a bottom surface of the head and comprising a pointed tip opposite the head. Once the IOL is positioned relative to the pupil, the helical-shaped coil fastener is configured to be applied to a distal end of each haptic to penetrate the anterior surface of the iris at an oblique angle, thereby affixing the IOL relative to the pupil. The helical-shaped coil fastener is configured to be affixed to the iris by rotatable penetration of the iris, and thus can be removed from the iris by reverse rotation of the helical-shaped coil fastener. The helical-shaped coil fastener has a low volume, large surface area, low cross-sectional area of penetration, and an oblique angle of penetration. Thus, the helical-shaped coil fastener is easy to apply, easy to remove, minimizes tissue damage, maximizes stability, and minimizes penetration force.

Additional embodiments disclosed herein are directed to other fasteners, IOLs, IOL assemblies, and methods to affix an IOL to an iris to correct for and astigmatism, with and without presbyopia vision correction. In this regard, some additional embodiments provide fasteners configured to engage an optic of an IOL to affix the IOL to the iris. These additional embodiments could also have one or more features to facilitate and/or control fastener penetration placement and/or penetration depth in affixing an IOL to an iris.

Figure 1B:
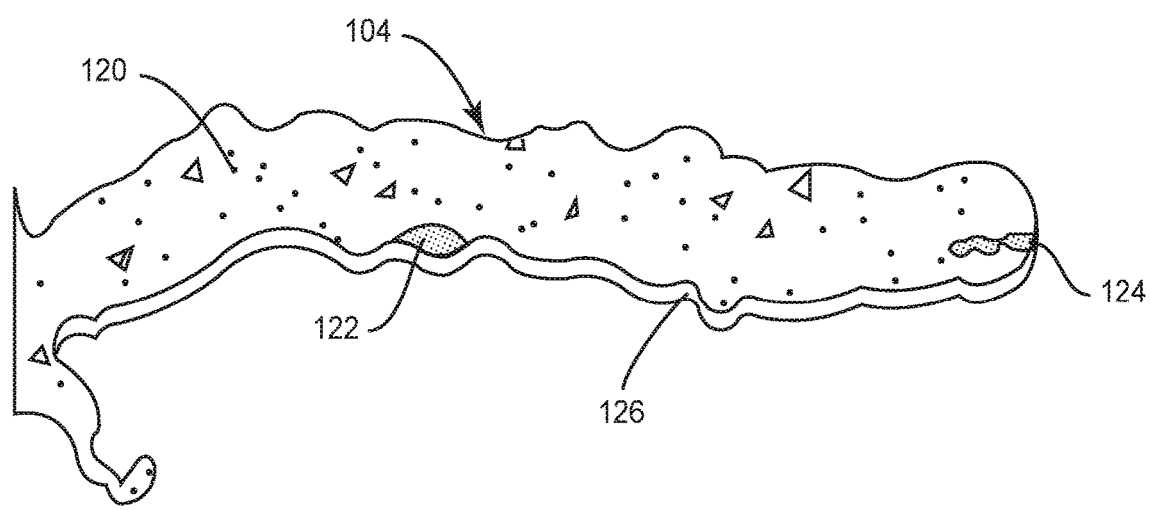
FIG. 1B is a cross-sectional view of half of the iris of FIG. 1A.
Figure 2A:
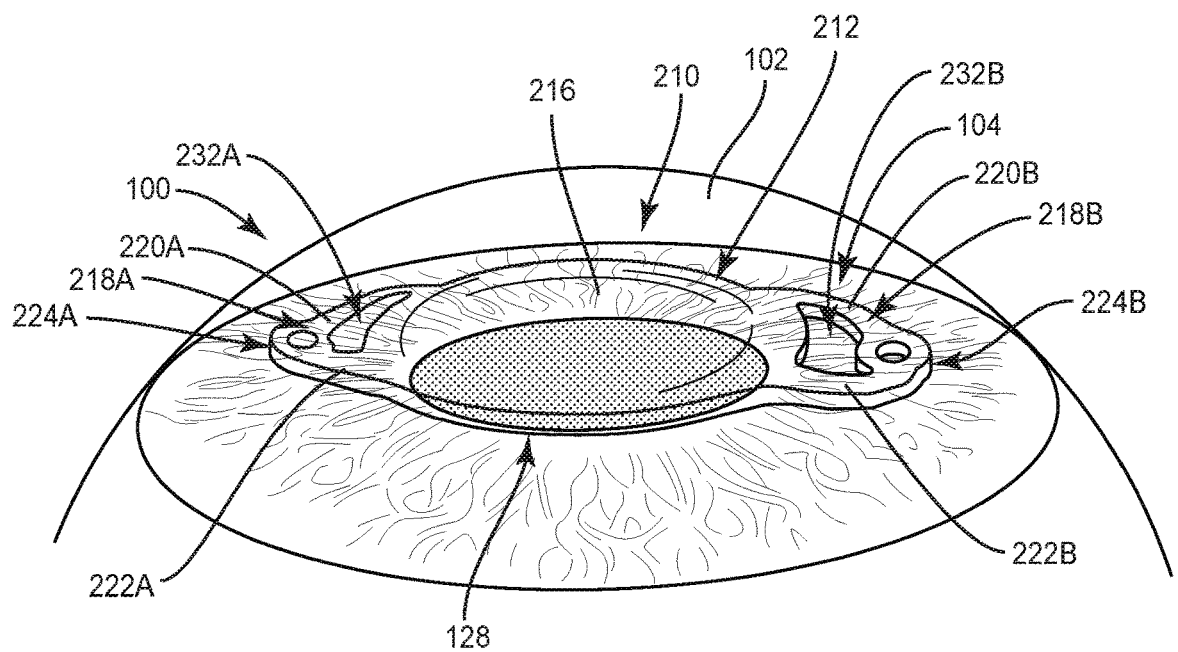
FIG. 2A is a top perspective view of an exemplary intraocular lens assembly (IOL assembly) comprising an exemplary intraocular lens (IOL) comprising an exemplary optic, at least one haptic for fixating the IOL to the iris of an eye, and an exemplary helical-shaped coil fastener configured to engage with the haptic to affix the IOL to the iris.

Before discussing intraocular implant assembly configured to be implanted into an eye to provide correction starting at FIG. 2A, a brief description of the human eye is provided with regard to FIGS. 1A and 1B.

In this regard, FIGS. 1A and 1B are views of a human eye. More specifically, FIG. 1A is a cross-section view of the human eye, and FIG. 1B is a cross-section view of half of the iris of the human eye of FIG. 1A. The human eye 100 comprises a cornea 102, an iris 104, a sclera 106, a vitreous 108, an anterior chamber 110, a chamber angle 112, a trabecular meshwork 114, a posterior chamber 116 and a human crystalline lens 118. Turning to FIG. 1B, the iris 104 controls the amount of light entering the eye 100 and is comprised of a stroma 120, a dilator muscle 122 and a sphincter muscle 124, which are tied together beneath the iris 104 by a pigment epithelium 126. The dilator muscle 122 and the sphincter muscle 124 are connected together via nerves which run through the pigment epithelium 126 and iris stroma 120 and which, as a group, operate to control the diameter of a pupil 128 (e.g., iris opening, pupil opening). Further, the pigment epithelium 126 constitutes approximately five percent (5%) of the total thickness of the iris 104. The opening and closing of the iris 104 is controlled by the sphincter muscle 124 and the dilator muscle 122, which are functionally interconnected beneath the iris 104 by the pigment epithelium 126 and nerves and nerve endings which are present therein. It is noted that nourishment is transferred to the iris 104 from the iris root through the iris 104.

While the diameter of the iris 104 will vary with the size of the eye 100 between individuals, the distance from the edge of the pupil 128 to the leading edge of the dilator muscle 122 is similar in size for all mature human eyes. Further, the dilator muscle 122 and sphincter muscle 124 are not directly connected together, and the iris tissue between the muscles 132, 134 does not move; thereby providing an ideal location to attach an intraocular implant assembly (discussed in more detail below) inside the eye 100 while not disturbing the natural working of the eye 100. In view of the foregoing, so long as the attachment means is positioned between the sphincter muscle 124 and the dilator muscle 122 and does not penetrate through iris 104, the eye 100 will experience minimal trauma over both the short and long terms, and the implant assembly should be well tolerated. Thus, penetration of between five percent (5%) and ninety-five percent (95%) of the iris 104 should securely attach the intraocular implant assembly to the iris 104 while not disturbing the nerves in the bottom five percent (5%) where the pigment epithelium 126 is located.

While the above description makes specific reference to the human eye 100, it will be understood that the apparatuses and methods described herein may be applied to various animals. For example, mammals such as dogs, cats and horses and the like may suffer injuries when their eyesight deteriorates with age, and vision correction surgery disclosed herein may prevent injury and thus extend their useful life.

Figure 2B:
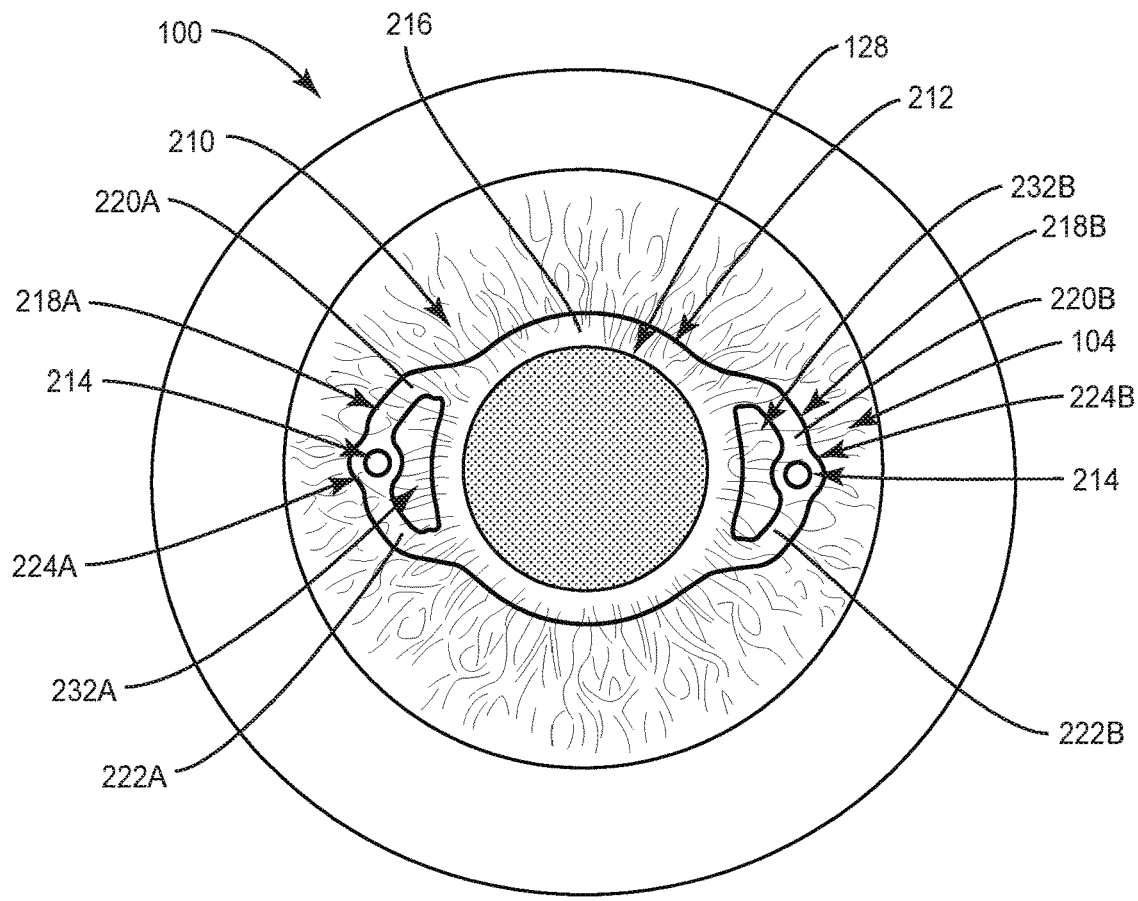
FIG. 2B is a top view of the IOL assembly and an eye of FIG. 2A.
Figure 2C:
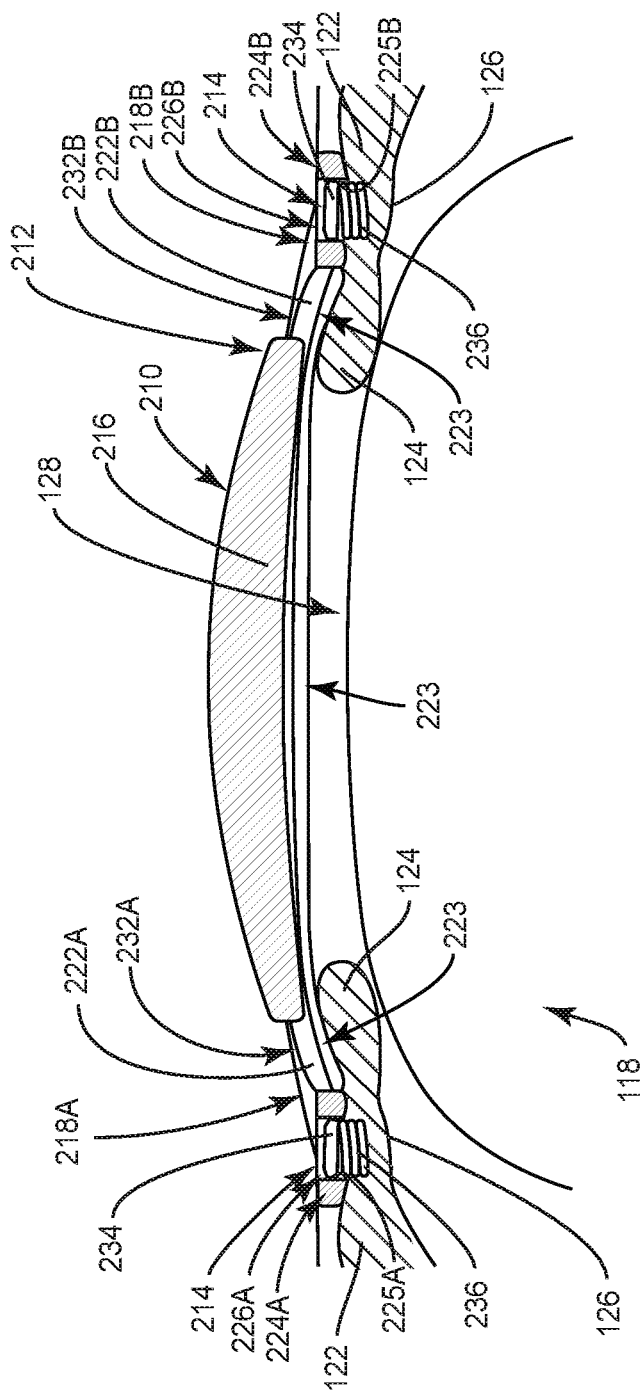
FIG. 2C is a side view of the IOL assembly and the eye of FIG. 2A.

FIGS. 2A-2G are views of an exemplary intraocular implant assembly. As shown in FIGS. 2A-2C, an IOL assembly 210 is provided that is configured to be implanted within the eye 100 (e.g., human, mammalian, etc.) for use with or without the crystalline lens 118. The IOL assembly 210 comprises an IOL 212 and one or more helical-shaped coil fasteners 214. The helical-shaped coil fasteners 214 affix the IOL to the eye 100 and provide low volume, large surface area, low cross-sectional area of penetration, and an oblique angle of penetration. Thus, the helical-shaped coil fastener 214 is easy to apply, easy to remove, minimizes tissue damage, maximizes stability, and minimizes penetration force. The IOL 212 comprises an optic 216, a left haptic 218A extending from a left peripheral edge of the optic 216, and a right haptic 218B extending from a right peripheral edge of the optic 216 (the left and right haptics 218A, 218B vaulting the optic 216 away from the anterior surface of the iris 104). The optical characteristics of the IOL 212 of the IOL assembly 210 can work with the human optical system (i.e., cornea 102 and human crystalline lens 118) to correct for errors such as myopia, hyperopia, presbyopia, and astigmatism. The IOL 212 of the present disclosure is characterized by minimal tissue contact area of contact with the iris 104 (e.g., of less than 7 square mm and preferably between 1.5 and 5.0 square mm) and the ability to be easily inserted and removed with minimal trauma to eye tissues.

The optic 216 is generally circular and has an anterior side (e.g., closer to the eye 100), a posterior side (e.g., further from the eye 100), and an outer peripheral edge. The diameter of the optic 216 could be in the range of approximately 5 mm to 7 mm. In addition, the optic 216 can have varying anterior and posterior curvatures, depending on whether myopia or hyperopia is being corrected. Further curvature variations are added for the correction of cylinder (astigmatism), presbyopia, bi-focal or multi-focal and incorporate ashperization, extended range of focus or vision, and refractive or defractive optics. The characteristics of the particular optic 216 selected are left to the surgical judgment of the physician performing the implant procedure.

To facilitate fixation of the IOL 212 to an iris for anterior fixation, one or more haptics 218A, 218B are connected to the optic 216. The haptics 218A, 218B extend outward from the optic 216 and are circumferentially spaced apart from each other (around the peripheral edge of the optic 216). The left haptic 218A comprises a left first riser section 220A (e.g., left first arm, left first vaulted section) and a left second riser section 222A (e.g., left second arm, left second vaulted section). The left first riser section 220A extends from a left peripheral edge of the optic 216 (e.g., at a proximal end of the left first riser section 220A) to a left foot section 224A of the haptic 218A (e.g., at a distal end of the left first riser section 220A). Similarly, the left second riser section 222A extends from the left peripheral edge of the optic 216 at a proximal end of the left second riser section 222A to the left foot section 224A of the haptic 218A. The left first riser section 220A and left second riser section 222A are attached at opposite ends of the left foot section 224A. This arrangement creates a left aperture 232A between the left peripheral edge of the optic 216 and the left foot section 224A.

Similarly, the right haptic 218B comprises a right first riser section 220B (e.g., right first arm, right first vaulted section) and a right second riser section 222B (e.g., right second arm, right second vaulted section). The right first riser section 220B extends from a right peripheral edge of the optic 216 (e.g., at a proximal end of the right first riser section 220B) to a right foot section 224B of the haptic 218B (e.g., at a distal end of the right first riser section 220B). Similarly, the right second riser section 222B extends from the right peripheral edge of the optic 216 at a proximal end of the right second riser section 222B to the right foot section 224B of the haptic 218B. The right first riser section 220B and right second riser section 222B are attached at opposite ends of the right foot section 224B. This arrangement creates a right aperture 232B between the right peripheral edge of the optic 216 and the right foot section 224B.

Accordingly, each of the riser sections 220A, 222A, 220B, 222B comprise a proximal end, a distal end, and an intermediate section therebetween. The riser sections 220A, 222A, 220B, 222B project downwardly and away from the posterior side of the optic 216 in order to vault the IOL 212 and riser sections 220A, 222A, 220B, 222B away from the iris 104 to minimize tissue contact and provide a vault space 223 between the underside of the IOL 212 and the anterior surface of the iris 104 (e.g., the left and right foot sections 224A, 224B are positioned at a different height than the optic 216). The proximal ends and distal ends of the haptic riser sections 220A, 222A, 220B, 222B maintain the optic 216 in spaced relation from the iris 104. In other words, the left and right haptic foot sections 224A, 224B support the IOL 212 on the anterior surface of the iris 104, and the left and right haptic foot sections 224A, 224B are the only portion of the IOL 212 that contacts the iris 104. Minimizing surface contact of the IOL 212 with the iris 104 reduces aggravation, irritation, and trauma of the iris 104. Smaller projections, points, bumps, or ridges on the posterior surface of the haptic foot that become the contact points on iris can be further used to minimize the surface contact area of the haptic to iris.

As shown in FIG. 2C, the left haptic foot section 224A comprises an inner wall 225A defining a cavity 226A (e.g., fastener receptacle, coil receptacle, hole, engagement hole, aperture, opening, etc.) that extends downwardly from a posterior surface of the foot section 224A. The helical-shaped coil fastener 214 is positioned within the foot section cavity 226A to secure the IOL 212 to the iris 104 (as discussed in more detail below). Similarly, the right haptic foot section 224B comprises an inner wall 225B defining a cavity 226B (e.g., hole, aperture, opening) that extends downwardly from a posterior surface of the foot section 224B. The helical-shaped coil fastener 214 is positioned within the foot section cavity 226B to secure the IOL 212 to the iris 104 (as discussed in more detail below).

Wherever reference is made to the left haptic 218A (and parts thereof) in the description herein, the description could also be applied to the right haptic 218B (and parts thereof), and vice-versa.

The haptics 218A, 218B could be constructed with mechanical detents or threads that prevent the inadvertent advancement of the helical-shaped coil fastener 214 into the iris tissue, control the advancement or screwing process for the helical-shaped coil fastener 214, and/or prevent the helical-shaped coil fastener 214 from inadvertently disengaging (e.g., unscrewing unless engaged by a driver of a medical instrument). Further, on the posterior surface of the haptics 218A, 218B, one or more small protrusions, points, bumps, and/or ridges could act as legs to prevent any rocking motions for the IOL 212 while providing minimal surface area contact to the iris 104 (as opposed to the posterior surface of the IOL haptics 218A, 218B contacting the iris 104).

The optic 216 and the haptics 218A, 218B must be made of a material which is biologically inert, and the optic 216 must additionally be made of a material which satisfies the necessary optical and surgical insertion requirements. The term "biologically inert" is generally understood in the art to be a material which is not absorbed by the body fluids and which does not cause any adverse reaction when implanted. Commonly used materials, alone or in combination, for IOLs are, inter alia, silicone, acrylic, collagen, hydrogel and polymethylmethacrylate. Other suitable materials may include ophthalmic glass, quartz and other polymeric materials.

Figure 2D:
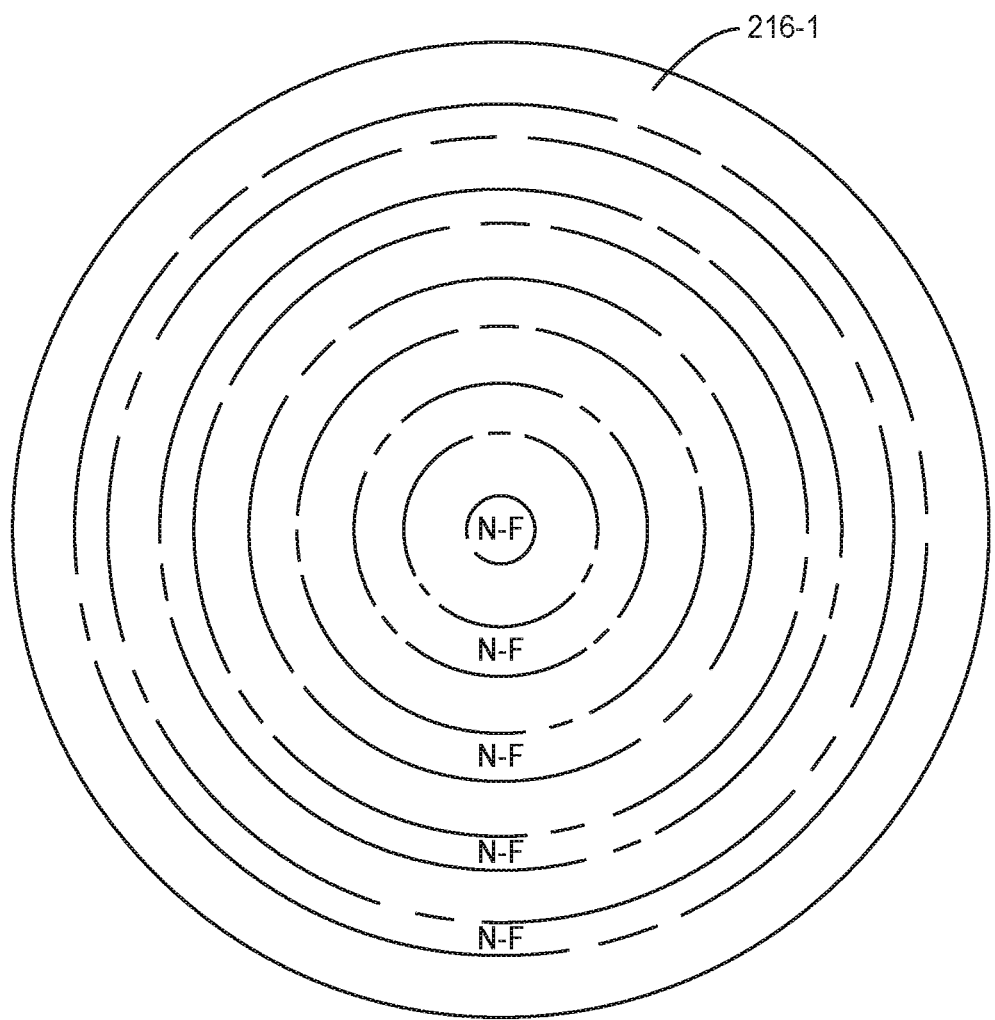
FIG. 2D is a top view of the optic of the IOL assembly similar to the IOL assembly in FIG. 2A, but with an optical having multiple correction powers and/or multiple types of correction powers within a single unitary optic.
Figure 2E:
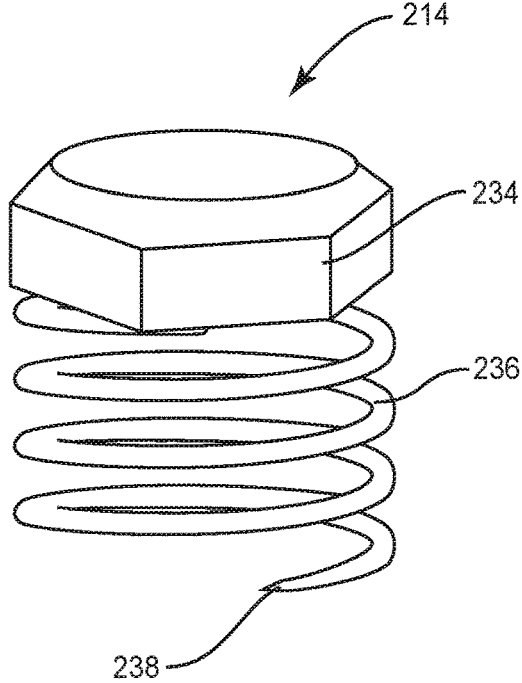
FIG. 2E is a top perspective view of a helical-shaped coil fastener of FIG. 2A.

As shown in FIG. 2D, an alternative optic 216-1 similar to optic 216 could be provided, but that has multiple correction powers and/or multiple types of correction powers within a single unitary optic 216 which could be concentrically positioned. These corrective powers could be derived using refractive optics, defractive optics, aspherizied optics, and extended range of focus or vision optics to correct for astigmatism or presbyopia and/or myopia or hyperopia The optic 216-1 could have an optical effect (e.g., a first optical effect) to correct for astigmatism and/or myopia or hyperopia. The optic 216-1 could also have another optical effect (e.g., a second optical effect) to address presbyopia (e.g., working in combination with crystalline lens at up to 2.0 diopter). The first optical effect and second optical effect could be concentrically positioned around a center of the optic 21, could be repeated (e.g., as in a concentric alternating pattern), and/or could vary in band thickness. The IOL 212 could be used as a phakic implant (e.g., for use with the crystalline lens) or as an aphakic implant (e.g., for use without the crystalline lens).

The optics 216, 216-1 may be implanted to supplement the natural (or implanted) lens or replace the natural lens. For procedures where the optic 216, 216-1 are configured to work with the natural human lens (left in place), the optics 216, 216-1 can be selected to produce the preselected optical effect, e.g., myopia of +1 diopter to +30 diopter, hyperopia of −1 diopter to −20 diopter, astigmatism of +/−1 diopter to +/−8 diopter at up to +/−180 degrees, and presbyopia of 0.5 diopter to 2 diopter, or 2.5 diopter to 4 diopter. For procedures where the optics 216, 216-1 are configured to work without the natural human lens (removed), the optics 216, 216-1 can be selected to produce the preselected optic effect, e.g., myopia of +1 to +30, hyperopia of −1 to −20, astigmatism of +/−1 diopter to +/−8 diopter at up to +/−180 degrees, and presbyopia of 0.5 diopter to 2 diopter, or 2.5 diopter to 4 diopter. The optics 216, 216-1 could include one or more optical features which could be concentrically positioned, such as refractive features (e.g., a refractive lens), defractive features, multifocal features (with different focal lenses concentrically positioned), bifocal features (with different focal lenses contentrically positioned), aspherized features, extended range of focus or vision, etc.

The natural human lens provides some amount of accommodation even when presbyopia is present. The accommodation provided by the natural human lens is additive with the presbyopia correction power provided in the IOL 212. By providing presbyopia correction via an IOL 212 adapted to work in combination with the human lens, less presbyopia correction power (i.e., diopters) may be needed to correct presbyopia. Limiting the presbyopia correction power is advantageous since non-desired optical effects increase non-linearly for a given increase in diopter power. The optics 216, 216-1 could address refraction to correct distance errors when providing presbyopia correction. In this manner, providing the presbyopia correction power does not increase refractive distance error. For example, if refractive error is increased, distance error is increased thus increasing an existing myopia or hyperopia, which may then cause a need for additional correction, such as through glasses for example. With the IOL 212, the refractive correction can be used to take a patient to emetropia (i.e., no refractive distance error). Thus, the presbyopia correction power would not add to the refractive distance error. Note that any further discussion of optic 216 below can include the optic 216-1 in FIG. 2D.

As shown in FIGS. 2C-2G, the helical-shaped coil fastener 214 comprises a head 234 (e.g., top portion) and a helical wire 236 (e.g., coil, helical coil, spring coil, corkscrew, bottom portion, etc.) extending from a bottom surface thereof. The helical-shaped coil fastener 214 anchors the IOL 212 to the iris 104. The helical wire 236 (e.g., helical coil) includes a top end (not shown) extending from a bottom surface of the head 234 and a pointed tip 238 (e.g., leading tip) at a bottom end thereof. The width of the head 234 (e.g., head width) could be wider, smaller, or the same size as a helical diameter of the helical wire 236. The helical-shaped coil fastener 214 reduces trauma to iris tissue and allows the iris tissue to return to its native state after removal thereof. For example, compared to a threaded screw, the helical-shaped coil fastener 214 could have the same depth penetration, increased surface area, decreased penetrated volume, and decreased penetrating cross-sectional area. The increased surface area of the helical-shaped coil fastener 214 provides more surface area to spread out the retention force (reducing risk of accidental detachment or tearing of the iris 104). Unlike a screw, the helical-shaped coil fastener 214 does not have to rely on threads for retention and requires little axial force for penetration and insertion. More specifically, the helical-shaped coil fastener 214 has accommodative properties that resist transmitting forces from the IOL 212 to the iris tissue or from the iris tissue to the IOL 212. This flexibility is particularly useful in dynamic environments and conditions, regardless of whether a pullout force is applied perpendicular or at an angle (e.g., 45 degrees) to the iris tissue plane or whether vibratory or rotational forces are concurrently applied. By comparison, screws and similar attachments are more susceptible to lower pull out forces within vibratory or rotational pull out forces.

Additionally, the helical-shaped coil fastener 214 is self-guiding. The helical-shaped coil fastener 214 can be made from stainless steel, spring steel, Elgiloy, super elastic materials (e.g., nitinol), titanium, or a polymer (e.g., nylon, polypropylene, acrylic, PEEK (polyether ether ketone), PET (polyethylene terephthalate), etc.), or other biocompatible material (e.g., with a suitable stability profile for implantation). In particular, super elastic materials (e.g., nitinol) can withstand great deformation without yielding.

The head 234 and/or helical wire 236 of the helical-shaped coil fastener 214 can be configured (e.g., sized and/or shaped) to fit within the IOL haptic cavity 226A, 226B, such that the circumference and/or diameter of the helical wire 236 can be slightly smaller than that of the IOL haptic foot section cavity 226. Further, after the circumference of the helical wire 236 penetrates the iris tissue and exits the posterior surface of the IOL 212, the circumference and/or diameter of the helical wire 236 can sweep out (e.g., enlarging the circumference and/or diameter) such that the circumference and/or diameter of the helical wire 236 is larger than that of the IOL haptic cavity 226A, 226B. The circumference of the helical wire 236 can vary from a tapered coil shape to a larger coil. In an alternative embodiment, the helical wire 236 can be sized to fit within mating treads or grooves within the IOL haptic cavity 226A, 226B. For example, the IOL haptic cavity 226A, 226B could be molded with internal threads.

The helical-shaped coil fastener 214 is configured to penetrate a portion of but less than the entire iris 104 (e.g., one half the thickness of the iris 104) to avoid penetrating the pigment epithelium 126. The amount of penetration and contact area could vary with the mass of the IOL, the number and structure of haptics 218A, 218B, optic 216 to haptic 218A, 218B vaulting, and/or other factors. It is noted that the helical-shaped coil fasteners 214 are of sufficient length so as to avoid interfering with proper iris function ((e.g., the muscles (dilator muscle 122 and sphincter muscle 124) which control the opening and closing of the pupil 128)).

The helical wire 236 of the helical-shaped coil fastener 214 minimizes the cross-sectional area (e.g., cross-sectional profile) at insertion and/or removal, which also reduces the force required to penetrate and engage the iris 104. Further, the helical wire 236 provides good shock absorption. Additionally, the pointed tip 238 penetrates and enters the iris 104 at an oblique angle, thereby reducing the force required to penetrate and engage the iris 104 and to resist tearing of iris tissue. The rotational force of screwing in the helical-shaped coil fastener 214 reduces the axial insertion force required to penetrate the iris 104. Similarly, the helical-shaped coil fastener 214 can be unscrewed out of the iris tissue and retraces the insertion path to minimize tissue damage (e.g., reduce the possibility of tearing or disrupting the iris tissue). This is drastically improved compared with a screw, which penetrates tissue axially (not obliquely), requires large axial insertion force to start proper threading, and has a large cross-sectional area at insertion and/or removal. Additionally, the helical-shaped coil fastener 214 and/or anterior surface of the IOL 212 could include a mechanical interference feature (e.g., tab, platform, and/or other mechanical detent on the helical-shaped coil fastener head 234 and/or an anterior surface of the IOL 212) to prevent inadvertent rotation and dislodging of the helical-shaped coil fastener 214 from the iris tissue.

The head 234 of the helical-shaped coil fastener 214 helps to limit the maximum depth penetration of the helical-shaped coil fastener 214 and controls the amount of material of the helical-shaped coil fastener 214 placed into the iris 104 (e.g., to limit the posterior profile of the helical-shaped coil fastener 214). This reduces the potential to penetrate completely through the iris tissue since ideally the attachment mechanism increases retention force (e.g., purchase and anchorage) within the interstitial space of the iris 104. The head 234 could be flat and/or have a minimal profile. Additionally, the head 234 could have an engagement feature (e.g., members, slots, holes, ridges, protrusions, or other mechanical features) to accept a medical instrument supplying a rotational force. For example, for head engagement, the head 234 and driver of the medical instrument can mate by a peripheral edge (e.g., hexagonal-shaped head), mechanical detents (e.g., crosses, grooves, bumps, ridges, etc.), magnetic energy, vacuum energy, gripping force, etc. The head shape could be domed, flat, recessed into the helical wire 236, and/or formed by a top of the helical wire 236 itself (described below in more detail).

The helical wire 236 can be made from round wire, D-shaped wire, flat wire, or any multiple configurations of shapes. In some instances, a flat wire design can provide greater penetration and insertion force since the rectangular aspect of the flat wire resists side-to-side motions. A D-shaped wire can provide a lower profile for insertion within the tissue since the mass of the penetrating member within the tissue is reduced. The helical wire 236 could have a variety of pitch configurations including open (e.g., where each rotation of the coil is slightly apart) or closed (e.g., where each rotation of the coil is nearly touching the adjacent pitch). The pitch angle of the helical wire 236 can vary from 5 degrees to 45 degrees relative to the planar surface of the iris tissue. The pitch angle of the helical wire 236 can vary throughout the length or height of the helical wire 236. The pitch can change once it exits the posterior surface of the IOL 212 (described below in more detail). For penetration into iris tissue, the pointed tip 238 of the helical wire 236 could be tapered, diamond shaped, tipped with multiple flat edges or facets, have one flat edge, and/or have an eccentric tip, etc.

The helical-shaped coil fastener 214 could also be self-rotating. For example, the helical wire 236 can be made from a shape memory material that automatically coils or unspins into tissue once released. In the wound state, the helical wire 236 has potential energy. Once released, the helical wire 236 unwinds and threads into the iris tissue. In another embodiment, the helical wire 236 can be pre-loaded in the IOL haptic foot section cavity 226 in a pre-wound state. Once the IOL assembly 210 is placed into the anterior chamber 110 and positioned by the physician on the iris 104 in the proper location, the helical-shaped coil fastener 214 can be pushed downward through the IOL haptic foot section cavity 226. Once mechanically displaced, the helical wire 236 of the helical-shaped coil fastener 214 unwinds and thereby screws into the iris tissue.

Further, the helical wire 236 is spring-like and resilient and could provide benefits related to material fatigue. As the helical wire 236 is compressed or in tension, the shape and material properties are biased to return to their natural or annealed configuration. The helical wire 236 creates an attachment mechanism that behaves as a suspension system for the connection of the IOL 212 to the iris tissue. Forces that are imparted to the iris tissue could be dampened by the properties of the helical wire 236 to avoid transmitting the forces to the remainder of the IOL 212 or the contralateral attachment point on the IOL 212. The dampening properties can be created within a particular portion of the helical wire 236 so that less dampening properties are available for the portion of the helical wire 236 that threads into the iris tissue with a portion of greater dampening properties near or adjacent to the posterior surface of the IOL 212. The dampening portion of the helical wire 236 can be primarily within and about the haptic foot section cavity 226A, 226B. With a spring coil shape, the helical-shaped coil fastener 214 has dampening or shock absorbing properties that could help limit the forces imparted onto the IOL 212 from being transmitted to the iris tissue, or vice versa. The effect of dampening the forces through the attachment system could reduce the propensity for stress concentration and provide greater fatigue strength for the IOL.

Figure 2F:
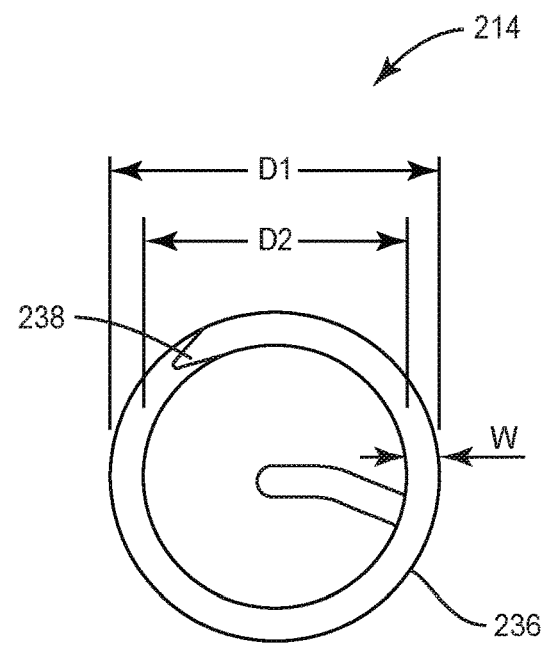
FIG. 2F is a bottom view of the helical-shaped coil fastener of FIG. 2A.

FIG. 2F is a bottom view of the helical-shaped coil fastener 214. The wire 236 of the helical-shaped coil fastener 214 has a wire diameter which is a width or thickness of the wire 236 itself. A helix formed from the wire 236 of the helical-shaped coil fastener 214 defines an outer diameter (e.g., helix diameter, coil diameter), and the wire 236 defines a generally cylindrical hollow center (e.g., inner aperture, void, etc.) having a second diameter (hollow center diameter). The IOL haptic foot section cavity 226A, 226B could have a haptic hole diameter. The dimensions of the helical-shaped coil fastener 214 and corresponding IOL haptic foot section cavity 226A, 226B could have a variety of dimensions. For example, the wire diameter (W) could be between 0.125-1 mm, the helix diameter (D1) could be between 1-3 mm, the hollow center diameter (D2) could be between 0.5-2.5 mm, and the haptic hole diameter could be between 1.0-3.0 mm. The helix depth (e.g., 0.5 to 3 mm depth) could be approximately the same size (or slightly less) than the haptic hole depth (e.g., 0.5 to 3 mm depth). The helix diameter could be approximately the same size (or slightly larger for a friction fit) than the haptic hole diameter. Smaller and larger wire diameters for the helical coil can be employed. Below is a table of dimensions for a number of different exemplary embodiments.

| Haptic Hole Diameter | Coil Diameter (D1) | Wire Diameter (W) | Hollow Center Diameter (D2) | Ratio of D1 to W |
|---|---|---|---|---|
| 1.0 mm | 1.0 mm | 0.125 mm | 0.75 mm | 8:1 |
| 1.0 mm | 1.0 mm | 0.25 mm | 0.5 mm | 4:1 |

-continued

| Haptic Hole Diameter | Coil Diameter (D1) | Wire Diameter (W) | Hollow Center Diameter (D2) | Ratio of D1 to W |
|---|---|---|---|---|
| 1.5 mm | 1.5 mm | 0.125 mm | 1.25 mm | 12:1 |
| 1.5 mm | 1.5 mm | 0.25 mm | 1.0 mm | 6:1 |
| 1.5 mm | 1.25 mm | 0.25 mm | 0.75 mm | 2:1 |
| 1.5 mm | 1.0 mm | 0.25 mm | 0.5 mm | 4:1 |
| 1.5 mm | 1.5 mm | 0.5 mm | 0.5 mm | 3:1 |
| 2.0 mm | 2.0 mm | 0.125 mm | 1.75 mm | 16:1 |
| 2.0 mm | 2.0 mm | 0.25 mm | 1.5 mm | 8:1 |
| 2.0 mm | 2.0 mm | 0.5 mm | 1.0 mm | 4:1 |
| 2.0 mm | 1.5 mm | 0.25 mm | 1.0 mm | 6:1 |
| 2.5 mm | 2.5 mm | 0.125 mm | 2.25 mm | 20:1 |
| 2.5 mm | 2.5 mm | 0.25 mm | 2.0 mm | 10:1 |
| 2.5 mm | 2.5 mm | 0.5 mm | 1.5 mm | 5:1 |
| 2.5 mm | 2.5 mm | 1.0 mm | 0.5 mm | 5:2 |
| 3.0 mm | 3.0 mm | 0.125 mm | 2.75 mm | 24:1 |
| 3.0 mm | 3.0 mm | 0.25 mm | 2.5 mm | 12:1 |

Figure 2G:
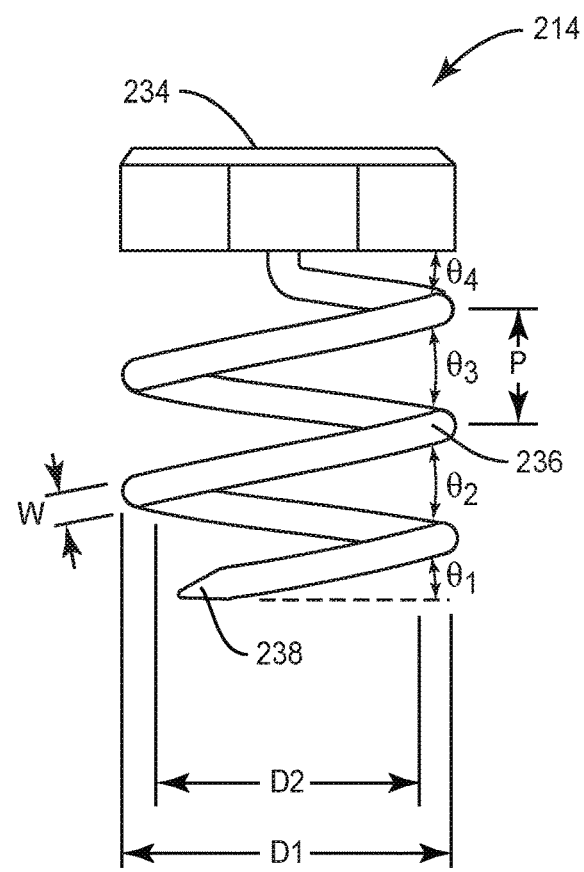
FIG. 2G is a side view of the helical-shaped coil fastener of FIG. 2A.

FIG. 2G is a side view of the helical-shaped coil fastener 214. As shown, the wire 236 of the helical-shaped coil fastener 214 includes a pitch (P). The pitch could vary depending upon the desired depth of penetration, the angle of penetration, retention force requirements, etc. Further, the pitch could be constant or variable (e.g., to increase the retention force of the helical-shaped coil fastener 214 within the iris 104). As shown, each coil turn of the wire 236 defines a different angle ($\theta$). More specifically, a first angle ($\theta_1$) defines the angle of penetration of the pointed tip 238 and the anterior surface of the iris 104. A second angle ($\theta_2$) defines the angle between a first coil turn and a second coil turn, and a third angle ($\theta_3$) defines the angle between the second coil turn and a third coil turn. A fourth angle ($\theta_4$) defines the angle between the third coil turn and a bottom surface of the helical-shaped coil fastener head 234. The first angle ($\theta_1$) and fourth angle ($\theta_4$) could be about the same, and/or the second angle ($\theta_2$) and third angle ($\theta_3$) could be about the same. Alternatively, they could be different (e.g., if the pitch of the wire 236 is variable). The helical-shaped coil fastener 214 increases its retention force within the iris 104 (e.g., interstitial space) with each subsequent coil turn rotatably inserted into the iris 104.

In another embodiment (not shown), the helical-shaped coil fastener 214 can connect the IOL 212 to the iris tissue such that the IOL 212 floats above the iris tissue and/or has minimal contact points with the iris tissue. In other words, the haptic foot section 224A, 224B would not contact the anterior surface of the iris 104, thereby reducing the impact (e.g., overall surface contact area) of the IOL 212 on the iris 104. In this way, the helical wire 236 could create a predetermined distance or space between the iris 104 and the posterior surface of the IOL 212. This could be accomplished in conjunction with tabs or a vaulted portion of the IOL haptic 218A, 218B that would be directly above the anterior surface of the iris 104.

FIGS. 3A-3E are views illustrating an exemplary surgical insertion and fixation of the intraocular implant assembly that can be used to surgically insert and affix the IOL 212 in FIGS. 2A-2G for example.

Figure 3A:
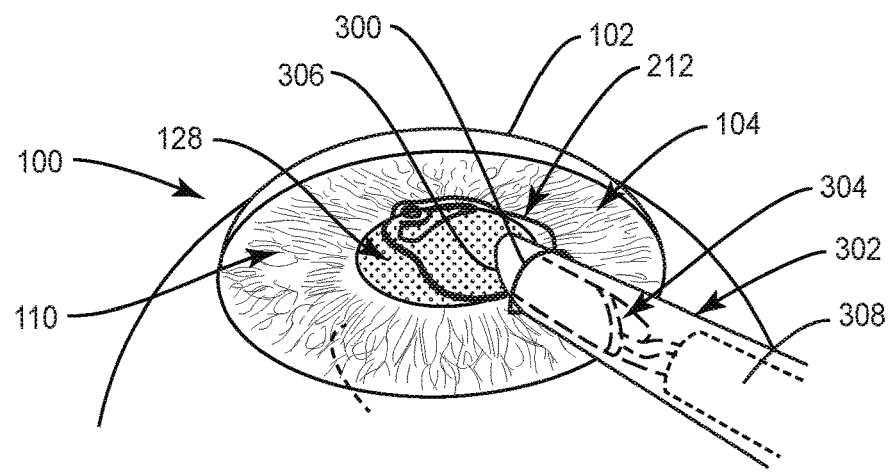
FIG. 3A is a top perspective view of a step in an exemplary surgical method for treating an eye condition in a human with an IOL assembly, the IOL assembly comprising an IOL and a helical-shaped coil fastener of FIGS. 2A-2G, and more specifically, the top perspective view illustrates surgical insertion of the IOL within an eye.

As shown in FIG. 3A, a small incision 300 (e.g., between 1.8 mm and 4.0 mm, etc.) is made in the cornea 102 or sclera 106 of the eye 100 (e.g., by a physician or an ophthalmic surgeon). An inserter 302 (e.g., insertion instrument, IOL shooter, etc.) defining a channel 304 and having an angled peripheral edge 306 at a distal opening is then inserted into the incision 300. The angled peripheral edge 306 facilitates penetration of a portion of the inserter 302 through the incision 300. The inserter 302 further comprises a piston 308 within the channel 304. The channel 304 of the inserter 302 contains a folded (e.g., deformed, bent, rolled, etc.) IOL 212 within the channel 304, positioned closer to the distal opening than the piston 308. Folding the IOL 212 reduces the overall insertion size of the IOL 212 and thereby minimizes the size of the incision 300 required.

Once the inserter angled peripheral edge 306 and/or a portion of the channel 304 has been inserted into the incision 300, the distal opening of the inserter 302 is positioned and roughly centered over the pupil 128. The piston 308 then translates towards the distal opening, thereby pushing the folded IOL 212 out of the distal opening into the anterior chamber 110 of the eye 100 (e.g., over the pupil 128). Once the IOL 212 is pushed into the anterior chamber 110, the IOL 212 naturally unfolds. The IOL 212 could be positioned within the channel 304 such that the anterior surface of the IOL 212 is aligned with the most distal point of the angled peripheral edge 306 of the inserter 302. This could facilitate proper orientation of the inserter 302 by the surgeon and ensure that when the IOL 212 unfolds, the posterior surface of the IOL 212 is proximate the anterior surface of the iris 104.

Figure 3B:
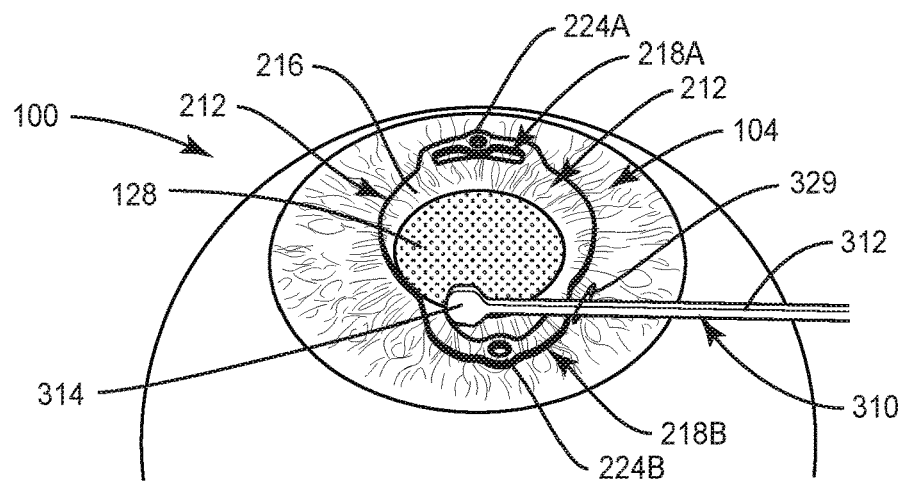
FIG. 3B is a top perspective view illustrating adjustment of the intraocular implant assembly within the eye.

In FIG. 3B, a paddle 310 or similar instrument (e.g., a hook, twisser, etc.) with a shaft 312 and a bulbous end 314 is used to position the IOL 212 within the anterior chamber 110 of the eye such that the IOL optic 216 is suitably positioned over the pupil 128 of the eye 100. More specifically, the bulbous end 314 is inserted through the incision 300 and contacts the IOL 212 to push, pull, and/or rotate the IOL 212 relative to the pupil 128. The IOL 212 is preferably oriented such that the IOL haptics 218A, 218B are oriented left to right on the patient's eye 100. As the IOL haptics 218A, 218B are oriented consistent with the natural eye opening (e.g., of the eyelids) of a patient, this facilitates implantation by the surgeon.

Figure 3C:
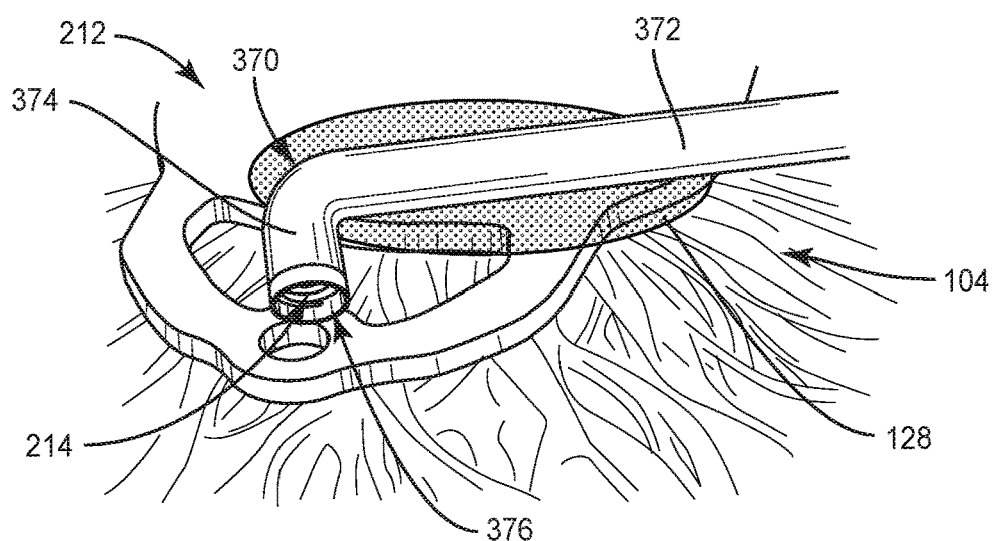
FIG. 3C is a top perspective view illustrating positioning an exemplary fastener applicator tool inserted in the eye relative to the IOL.

In FIG. 3C, once the IOL 212 is properly positioned within the eye 100, a distal portion of a fastener applicator tool 370 (discussed in more detail below) is inserted through the incision 300. More specifically, the fastener applicator tool 370 comprises a first cannula 372 and a second cannula 374 more distal than the first cannula 372 and approximately perpendicular to the first cannula 372. Preferably, the fastener applicator tool 370 is inserted through the incision 300 such that the second cannula 374 is aligned with the incision 300, thereby reducing the degree to which the incision 300 must spread to allow passage of the distal portion of the fastener applicator tool 370. The second cannula 374 comprises a distal opening 376. As shown, at least one helical-shaped coil fastener 214 is positioned within the fastener applicator tool 370, and more specifically, the helical-shaped coil fastener 214 is positioned within the second cannula 374 proximate the distal opening 376. However, the fastener applicator tool 370 could be preloaded with a plurality of helical-shaped coil fasteners 214.

Figure 3D:
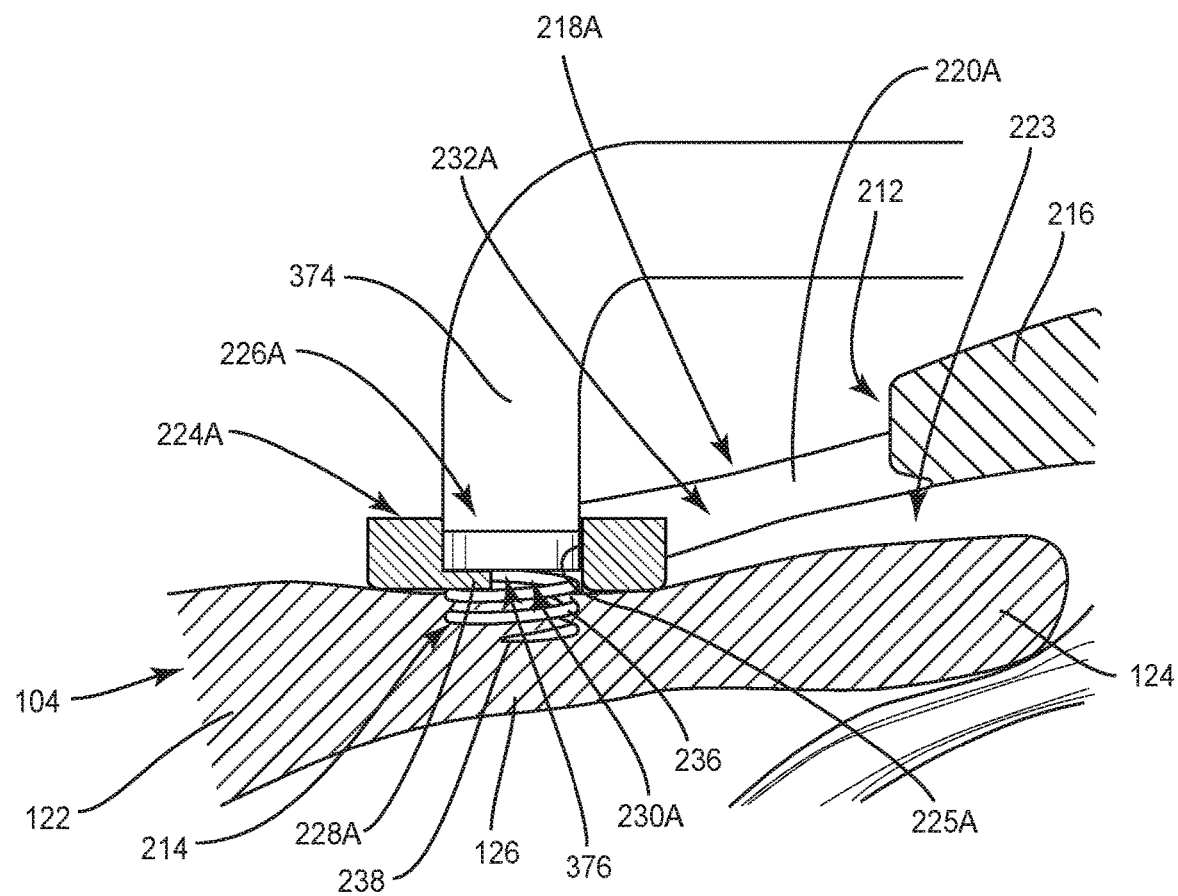
FIG. 3D is a cross-sectional side view of the fastener applicator tool in FIG. 3C applying a helical-shaped coil fastener to a haptic of an IOL.

In FIG. 3D, the distal opening 376 and at least a portion of the second cannula 374 could be inserted into the IOL left haptic foot section cavity 226A. The fastener applicator tool 370 then translates and rotates the helical-shaped coil fastener 214 through the distal opening 376 such that the pointed tip 238 of the helical-shaped coil fastener 214 penetrates the iris 104 (between the dilator muscle 122 and the sphincter muscle 124) and the helical-shaped coil fastener 214 engages (e.g., screws into) the iris tissue, but does not penetrate the pigment epithelium 126. Once the helical-shaped coil fastener 214 is fully engaged, the fastener applicator tool 370 is removed. Accordingly, the IOL 212 is attached to the iris 104 with a vault space 223 between the optic 216 and an anterior surface of the iris 104.

The fastener applicator tool 370 could be configured to rotate and translate the helical-shaped coil fastener 214 as it exits the distal opening of the fastener applicator tool 370. Alternatively, the IOL left haptic foot section inner wall 225A could be threaded (e.g., include mating threads), such that the fastener applicator tool 370 only translates the helical-shaped coil fastener 214 out of the distal opening, and the internal threads of the IOL left haptic foot section inner wall 225A rotate the helical-shaped coil fastener 214. Further, the fastener applicator tool 370 could be positioned over, but not inserted in, the IOL left haptic foot section cavity 226A.

As shown, the IOL left haptic foot section 224A includes a bottom wall 228A extending from the inner wall 225A into the cavity 226A proximate a posterior surface of the IOL haptic foot section 224A. A peripheral edge of the bottom wall 228A defines an opening 230A. Similarly IOL right haptic foot section 224B could also include a bottom wall 228A and opening (not shown). The helical wire 236 extends through the opening 230A to penetrate the iris 104. The fastener applicator tool 370 could facilitate the surgeon to ensure that the helical-shaped coil fastener 214 does not penetrate the bottom wall 228A. Alternatively, the helical-shaped coil fastener 214 could penetrate the bottom wall 228A. Further, the bottom wall 228A could extend throughout the entire bottom, such that an opening 230A is not defined, and the helical-shaped coil fastener 214 would have to penetrate the bottom wall 228A.

The haptics 218A, 218B could include one or more mechanical detents on a posterior surface of the haptic foot sections 224A, 224B to prevent rotation of the IOL 212 when screwing in the helical-shaped coil fastener 214. Additionally, or alternatively, the distal end of the fastener applicator tool 370 could have a mechanical detent (e.g., mechanical contact) that prevents the IOL 212 from moving when the helical-shaped coil fastener 214 is being screwed into the iris tissue. The mechanical detent could be shaped as a feature that receives the distal end of the fastener applicator tool 370 (similar to a hex shape or other non-circular shape). Additionally, or alternatively, distal end of the instrument could have a surface shaped to engage the IOL haptic inner wall 225A, 225B to prevent rotation or movement of the IOL 212 when the helical-shaped coil fastener 214 is being screwed into place. Additionally, or alternatively, a surface at a distal end of the fastener applicator tool 370 (and/or the IOL haptic inner wall 225A, 225B) could have a coefficient of friction that resists movement of the IOL 212. For example, a ring of silicone material around the circumference of the distal end of the fastener applicator tool 370 could be used. This silicone material could prevent movement of the IOL 212 when the helical-shaped coil fastener 214 is being screwed into place, present a non-traumatic or soft surface to the iris tissue as the leading edge of the distal end of the fastener applicator tool 370, and/or present a surface that would resist scratching the anterior surface of the IOL 212 if contacted by the distal end of the fastener applicator tool 370 during the process of intubating the IOL haptic foot section cavity 226A, 226B or the attachment process of placing the helical-shaped coil fasteners themselves.

Additionally, or alternatively, the helical-shaped coil fastener 214 could expand within the IOL haptic foot section cavity 226A, 226B once the helical-shaped coil fastener 214 has entered the iris tissue and the fastener applicator tool 370 been removed. More specifically, as opposed to screwing in the helical-shaped coil fastener 214 with threads on the IOL left haptic foot section inner wall 225A (and/or using a IOL left haptic foot section bottom wall 228A), the distal end of the fastener applicator tool 370 can intubate the IOL haptic foot section cavity 226A, 226B in at least a portion of the length thereof. The helical-shaped coil fastener 214 exits from the distal opening of the fastener applicator tool 370 and penetrates the iris tissue in a first configuration that is smaller than the interior diameter of the IOL left haptic foot section cavity 226A. After the helical-shaped coil fastener 214 is engaged with the iris 104, and after the fastener applicator tool 370 is removed from the helical-shaped coil fastener 214 and the IOL left haptic foot section cavity 226, at least a portion of helical wire 236 above the anterior surface of the iris 104 expands (or springs back into the IOL left haptic foot section cavity 226 from beneath the anterior surface of the iris 104) to assume a second configuration that is a larger diameter then the interior diameter of the IOL left haptic foot section cavity 226A to thereby contact the IOL left haptic foot section inner wall 225 and hold the IOL 212 in place. In this fashion, no downward forces are imparted to the IOL during the screwing process of the helical-shaped coil fastener 214. For this embodiment, the forces that the IOL 212 experiences are the radial expansion of the helical-shaped coil fastener 214 within the IOL left haptic foot section cavity 226A.

Figure 3E:
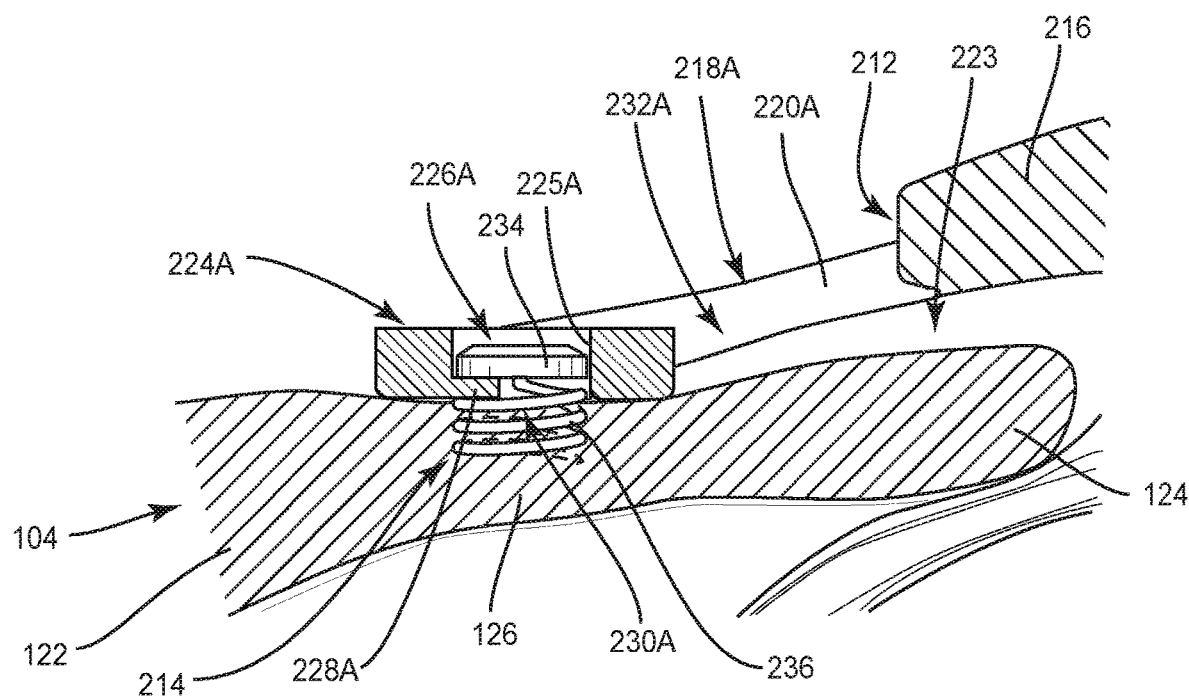
FIG. 3E is a cross-sectional side view of the helical-shaped coil fastener of FIG. 3D affixing the IOL to the iris.

In FIG. 3E, the helical-shaped coil fastener 214 is fully engaged with the IOL 212 and the iris 104. As shown, at least a portion of the helical wire 236 of the helical-shaped coil fastener 214 is engaged with the iris 104, and at least a portion of the IOL 212 (e.g., the IOL left haptic foot section bottom wall 228A) is compressed and secured between the helical-shaped coil fastener head 234 and an anterior surface of the iris 104. In this way, the helical-shaped coil fastener 214 is applied to each haptic 218A, 218B to secure the IOL 212 to the iris 104. Additionally, as shown, the IOL left haptic foot section 224A contacts the anterior surface of the iris 104, the IOL left haptic first riser section 220A vaults the IOL optic 216 away from the iris 104, and the IOL left haptic aperture 232A reduces the contact area of the IOL 212 (and the left haptic 218A) relative to the anterior surface of the iris 104. The IOL left haptic foot section opening 230A further reduces the contact area of the IOL left haptic foot section 224A with respect to the anterior surface of the iris 104.

Figure 4A:
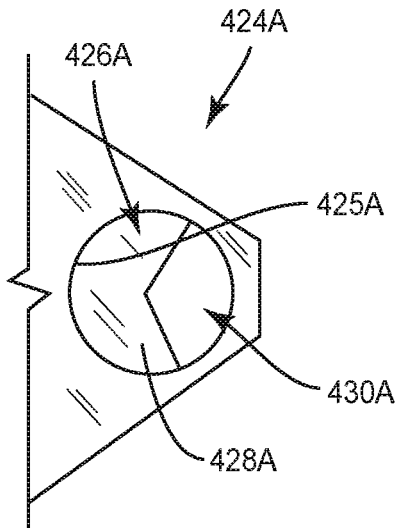
FIG. 4A is a top view illustrating an exemplary closed foot section cavity with a bottom wall at a distal end of a haptic of an IOL of the intraocular implant assembly.

As shown in FIG. 4A (and as described in FIGS. 2A-3E above), a haptic foot section 424A comprises an inner wall 425A defining a closed cavity 426A (e.g., hole, aperture, opening) that extends downwardly from an anterior surface of the foot section 424A. The closed cavity 426A could have a full circumference. The foot section 424A further includes a bottom wall 428A that extends inwardly into the closed cavity 426A from the inner wall 425A and proximate the posterior surface of the foot section 424A, or spaced a distance therefrom (e.g., to reduce the contact area of the haptic foot section 424A with the iris 104). The bottom wall 428A could partially or fully enclose the closed cavity 426A. If the bottom wall 428A fully encloses the closed cavity 426A (as in a blind hole), the helical-shaped coil fastener 214 would have to penetrate the bottom wall 428A to secure the IOL to the iris 104. If the bottom wall 428A partially encloses the closed cavity 426A, the peripheral edge of the bottom wall 428A and a portion of the inner wall 425A define an opening 430A extending upwardly from a posterior surface of the foot section 424A. A helical-shaped coil fastener 214 is positioned within the foot section closed cavity 426A to secure the IOL to the iris 104. The helical-shaped coil fastener head 234 contacts the bottom wall 428A to compress the bottom wall 428A between the helical-shaped coil fastener head 234 and the anterior surface of the iris 104. Also, of note, the helical-shaped coil fastener head 234 could be recessed and hidden within the haptic foot section 424A, such that at least a portion of the coil fastener head 234 does not extend past an anterior surface of the haptic foot section 424A.

Figure 4B:
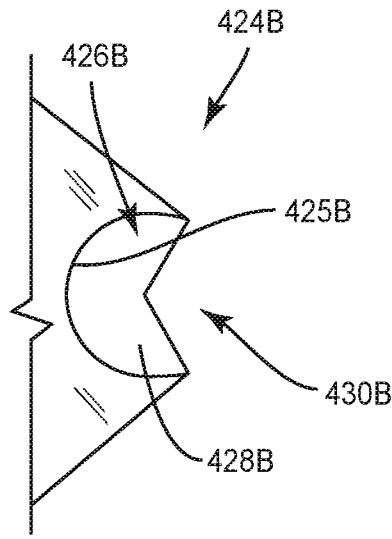
FIG. 4B is a top view illustrating another exemplary embodiment of an open foot section cavity with a bottom wall.

In FIG. 4B, the haptic foot section 424B comprises an inner wall 425B defining an open cavity 426B that extends downwardly from an anterior surface of the foot section 424B (similar to that of FIG. 4A). The inner wall 425B forms an arc (but not an enclosed circle), such that the open cavity 426B has a partial circumference. Such a design reduces the profile of the IOL 212 as well as the size of the IOL 212. Thus, the reduced haptic footprint also reduces the amount of contact area of the IOL 212 of the device to the anterior surface of the iris 104.

Figure 4C:
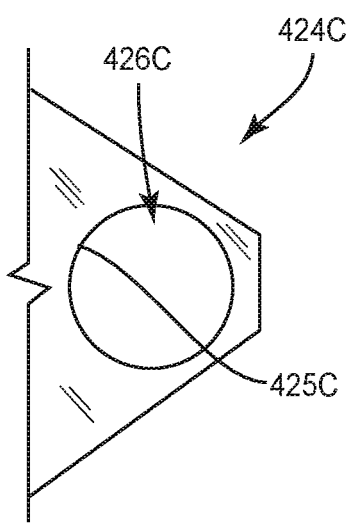
FIG. 4C is a top view illustrating another exemplary embodiment of a closed foot section cavity comprising a through hole.

In FIG. 4C, the haptic foot section 424C comprises an inner wall 425C defining a closed through hole 426C (similar to that of FIG. 4A, but without a bottom wall). This configuration may be used where the helical-shaped coil fastener head 234 is larger than the diameter of the through hole 426C, such that the helical-shaped coil fastener head 234 contacts the posterior surface of the haptic foot section 424C to compress the haptic foot section 424C between the helical-shaped coil fastener head 234 and the anterior surface of the iris 104. Alternatively, this could be used when the helical wire 236 has a diameter larger than the through hole 426C (e.g., a compression fit).

Figure 4D:
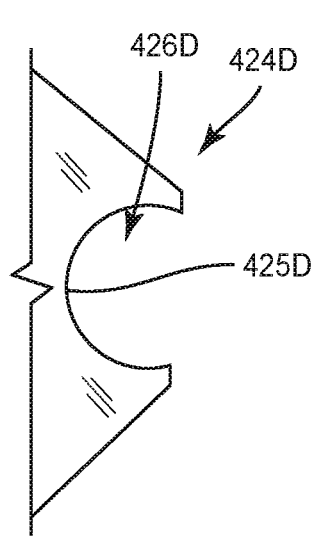
FIG. 4D is a top view illustrating another exemplary embodiment of an open foot section cavity comprising a through hole.

In FIG. 4D, the haptic foot section 424D comprises an inner wall 425D defining an open through hole 426D (similar to that of FIG. 4B but without a bottom wall). The haptic foot section 424D would operate similarly to that of FIG. 4C.

Figure 4E:
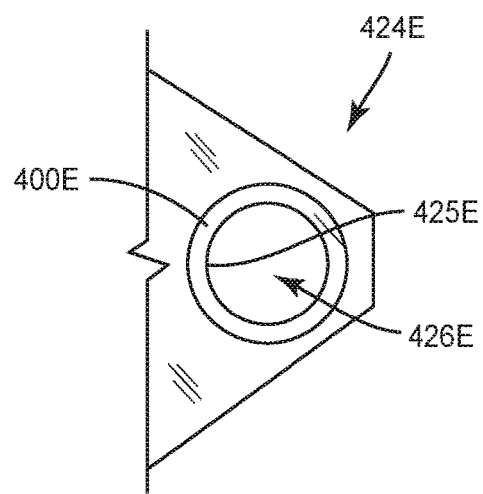
FIG. 4E is a top view illustrating another exemplary embodiment of a closed foot section cavity with a counter-bore hole.

In FIG. 4E, the haptic foot section 424E comprises an inner wall 425E defining a closed through hole 426E (similar to that of FIG. 4C), but the haptic foot section 424E further comprises a counterbore 400E so that the helical-shaped coil fastener head 234 is recessed within the haptic foot section 424E when fully engaged with the iris 104, thereby providing a smaller profile and hiding the helical-shaped coil fastener head 234 within the haptic foot section 424E, such that at least a portion of the coil fastener head 234 does not extend past an anterior surface of the haptic foot section 424E.

Figure 4F:
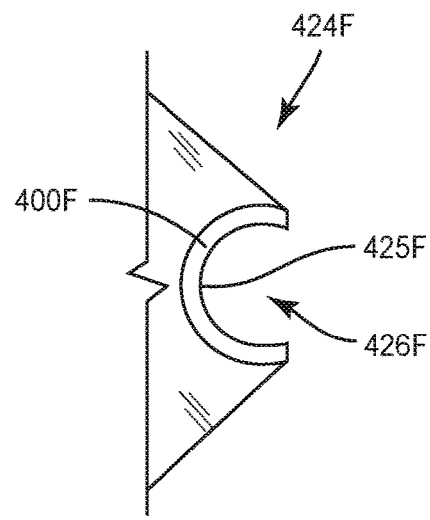
FIG. 4F is a top view illustrating another exemplary embodiment of an open foot section cavity with a counter-bore hole.

In FIG. 4F, the haptic foot section 424F comprises an inner wall 425F defining an open through hole 426F (similar to that of FIG. 4D), but the haptic foot section 424F further comprises a counterbore 400F. The haptic foot section 424F would operate similarly to that of FIG. 4E.

Figure 4G:
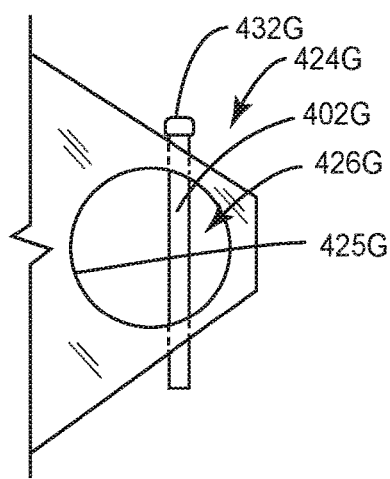
FIG. 4G is another exemplary embodiment of a closed foot section cavity with a retaining pin.

In FIG. 4G, the haptic foot section 424G comprises an inner wall 425G defining a closed through hole 426G (similar to that of FIG. 4C), but the haptic foot section 424G further comprises a retaining pin 402G (e.g., rod). The retaining pin 402G extends across the closed through hole 426G (e.g., across a diameter of the through hole 426G) and at least partially (but as shown completely) through the inner wall 425G to mount the pin 402G within the closed through hole 426G. One or both ends of the retaining pin 402G could include a cap 432G to prevent axial movement and potential accidental removal of the retaining pin 402G from the haptic foot section 424G. The retaining pin 402G could be located anywhere between the anterior and posterior surface of the haptic foot section 424G, but preferably toward the anterior surface. The retaining pin 402G could come preloaded in the haptic foot section 424G (along with a helical-shaped coil fastener 214) or could be inserted after the IOL 212 is deposited within the eye 100. In use, the helical-shaped coil fastener 214 could be inserted into the closed through hole 426G, before or after the retaining pin 402G has been mounted therein. The helical-shaped coil fastener 214 can translate through the closed through hole 426G with the retaining pin 402G positioned therein due to the spacing between the coil pitches of the helical wire 236. During insertion of the helical-shaped coil fastener 214 into the anterior surface of the iris 104 and after translating at least a portion of the closed through hole 426G, eventually the head 234 of the helical-shaped coil fastener 214 contacts the retaining pin 402G, and the IOL 212 is mounted to the iris 104 by downward compression of the helical-shaped coil fastener head 434 against a top surface of the retaining pin 402G, which also imparts downward compression of the haptic foot section 424G against the iris 104.

Figure 4H:
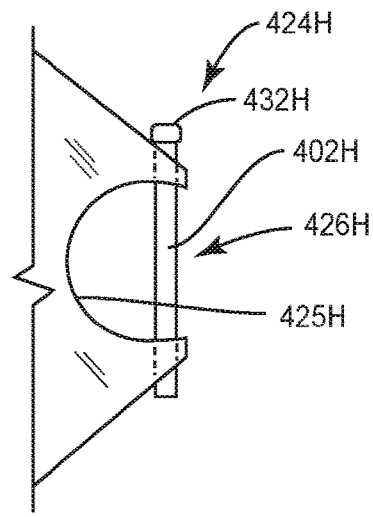
FIG. 4H is another exemplary embodiment of an open foot section cavity with a retaining pin.

In FIG. 4H, the haptic foot section 424H comprises an inner wall 425H defining an open through hole 426H (similar to that of FIG. 4D), but the haptic foot section 424H further comprises a retaining pin 402H. The retaining pin 402H would operate similarly to that of FIG. 4G and could include a cap 432H as described in FIG. 4G.

Figure 4I:
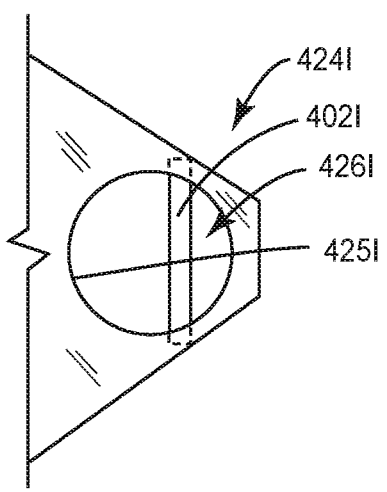
FIG. 4I is another exemplary embodiment of a closed foot section cavity with a retaining pin.

In FIG. 4I, the haptic foot section 424I comprises an inner wall 425I defining a closed through hole 426I (similar to that of FIG. 4G) with a retaining pin 402I (e.g., rod). The retaining pin 402I works similarly as that of retaining pin 402G of FIG. 4G, except ends of the retaining pin 402I are retained within the haptic foot section 424I (e.g., ends of the retaining pin 402I extend at least partially (but could extend completely) through the inner wall 425I to mount the retaining pin 402I within the closed through hole 426I.

Figure 4J:
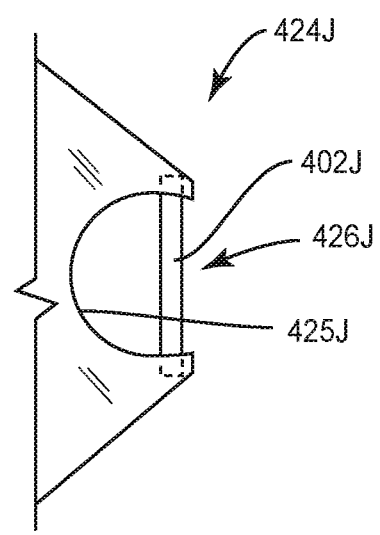
FIG. 4J is another exemplary embodiment of an open foot section cavity with a retaining pin.

In FIG. 4J, the haptic foot section 424J comprises an inner wall 425J defining an open through hole 426J (similar to that of FIG. 4I) with a retaining pin 402J. The retaining pin 402J would operate similarly to that of FIG. 4G.

In each of the embodiments discussed with respect to FIGS. 4A-4H, the cavity could be a straight or angled hole. More specifically, for a straight hole, the cavity could be configured perpendicular to a posterior surface of the haptic or with an axis normal thereto. In some embodiments, it may be advantageous for the cavity to be slightly angled (e.g., canted) relative to the posterior surface of the haptic, such as angled towards the pupil 128 (or iris periphery).

Figure 5A:
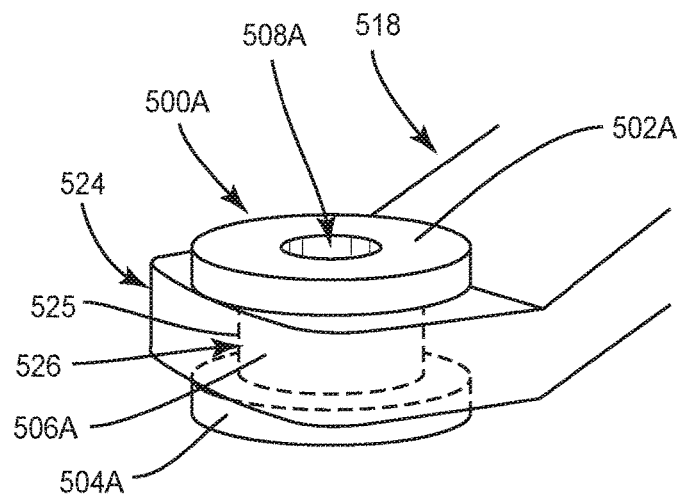
FIG. 5A is a side perspective view of a double-flange grommet attached to a distal end of a haptic of an IOL of an intraocular implant assembly, the double-flange grommet including a top flange and a bottom flange for attachment to the IOL before the IOL has been inserted into the eye.

FIGS. 5A-5D are views of another embodiment of the intraocular implant assembly incorporating a grommet. As shown in FIG. 5A, the double-flange grommet 500A includes an upper flange 502A (e.g., first flange), a lower flange 504A (e.g., second flange), and a shaft 506A therebetween, the upper flange 502A, lower flange 504A, and shaft 506A defining a channel 508A therein. Shown is a haptic 518 comprising a foot section 524 with an inner wall 525 defining a cavity 526. The double-flange grommet 500A would be pre-loaded in the haptic 518, such that the upper flange 502A is proximate an anterior surface of the IOL haptic foot section 524, the lower flange 504A is proximate a posterior surface of the IOL haptic foot section 524, and the shaft 506A is positioned within the haptic foot section cavity 526. As the diameter of the upper flange 502A and lower flange 504A is larger than the haptic foot section cavity 226, the double-flange grommet 500A is secure relative to the haptic foot section 224.

Incorporation of the double-flange grommet 500A could have benefits in the manufacturing process of the intraocular implant assembly since this component can be added onto the IOL after tumbling and polishing (e.g., as a final assembly step), which can occur after the optic has been lathed or molded (e.g., after precision and polished optics of the IOL are completed). During tumbling and polishing of the IOL, sharp and rough lens surfaces are removed. Hence mechanical detents, grooves, ridges, protrusions, and other mechanical features may be inadvertently altered or removed, or uncontrollably dimensioned. Insertion of the double-flange grommet 500A with such mechanical features (e.g., on a bottom surface of the lower flange 504A) within the haptic foot section cavity 226 as a secondary operation in the manufacturing process would ensure that the mechanical features are preserved without impacting the optic surface quality. As such, the optic surface itself would need to be protected during the grommet manufacturing step to not impact lens surface quality. The double-flange grommet 500A or other grommet can be added to the haptic hole configurations that employ a partial circumference, like shown in FIGS. 4C and 4F discussed above for example, such that the grommets 500A, 500B are inserted through the partial circumference to create a mechanical interference fit and attachment to the haptic.

Figure 5B:
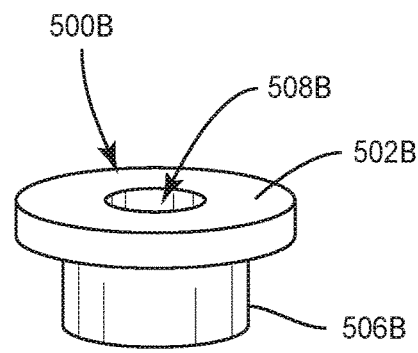
FIG. 5B is a side perspective view of an exemplary single-flange grommet, the single-flange grommet only including a top flange for attachment to the IOL after the IOL has been inserted into the eye.

As shown in FIG. 5B, the single-flange grommet 500B includes only an upper flange 502B and a shaft 506B extending downwardly therefrom (no lower flange), the upper flange 502B and shaft 506B defining a channel 508B. The single-flange grommet 500B could be inserted into a haptic foot section cavity after the IOL 212 is inserted into the anterior chamber 110 of the eye 100. This could provide structural rigidity to the haptic and provide an easier and more secure connection of the helical-shaped coil fastener 214 to the iris 104.

Figure 5C:
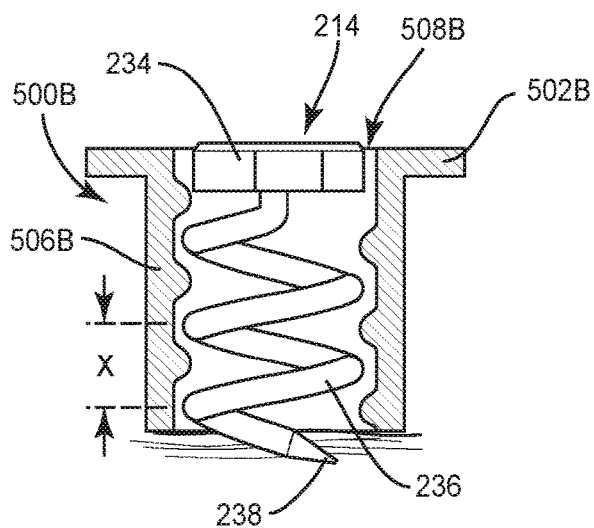
FIG. 5C is a cross-sectional side view of the single-flange grommet of FIG. 5B and a helical-shaped coil fastener, the helical-shaped coil fastener in a retracted orientation relative to the single-flange grommet.
Figure 5D:
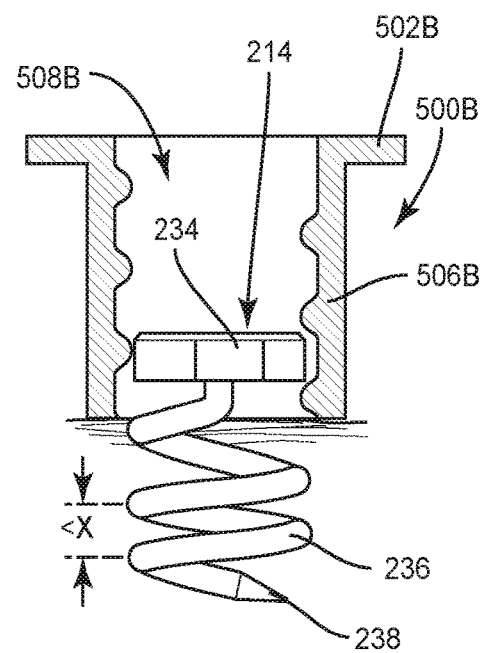
FIG. 5D is a cross-sectional side view of the single-flange grommet of FIG. 5B and the helical-shaped coil fastener, the helical-shaped coil fastener in an extended orientation relative to the single-flange grommet.

As shown in FIGS. 5C and 5D, the single-flange grommet 500B could receive a helical-shaped coil fastener 214 therein and serve as a housing mechanism for the helical-shaped coil fastener 214. The helical-shaped coil fastener 214 includes a head 234, helical wire 236, and pointed tip 238, as described above in FIG. 2E. As shown, a helical-shaped coil fastener 214 could be housed within the single-flange grommet 500B. The helical-shaped coil fastener 214 could be pre-loaded (e.g., prior to insertion into the eye) or installed after the IOL 212 is inserted into the eye 100. The single-flange grommet 500B and helical-shaped coil fastener 214 would serve as a nut and bolt within the haptic. An advantage of having the helical-shaped coil fastener 214 pre-loaded is that the helical-shaped coil fastener 214 is safely housed such that there is no danger of accidental damage (e.g., scraping, cutting, etc.) to the iris 104, or accidental damage to the IOL 212 (e.g., during insertion of the folded intraocular lens). In this way, to remove the helical-shaped coil fastener 214 from the iris, the helical-shaped coil fastener 214 is simply rotated in the opposite direction to translate the helical-shaped coil fastener back into the grommet 500A, 500B in a retracted orientation. The single-flange grommet 500B and helical-shaped coil fastener 214 contained therein can then be removed minimizing the risk of accidental injury to the eye 100 or IOL 212.

As shown in FIG. 5C, the helical-shaped coil fastener 214 is retained within the single-flange grommet 500B in a retracted orientation, and the internal threads thereof and helical-shaped coil fastener 214 are at a first pitch. The single-flange grommet 500B could include internal threads that serve as a mating piece for the pitches of the helical-shaped coil fastener 214. The thread pitch could have a take-off or exit that separates the pitch of the helical-shaped coil fastener 214 as it enters the iris tissue. Once entered into the tissue, the pitch of the helical-shaped coil fastener 214 would return to its natural state which would be a tighter pitch. Thus in practice, once screwed into the iris tissue, the helical-shaped coil fastener 214 would tighten once exited from the IOL 212 and directed into the tissue.

The single-flange grommet 500B may contain grooves, ridges, or mechanical features and protrusions that provide surfaces for the coil to reside, and may also serve as a mechanical detent to prevent over-treading of the helical-shaped coil fastener 214 into the iris tissue. The posterior surface of the single-flange grommet 500B may contain bumps, points, protrusions, or ridges to minimize the surface contact of the grommets 500A, 500B to the iris tissue.

As the helical-shaped coil fastener rotates and traverse the single-flange grommet channel 508B (or alternatively, a threaded haptic foot section cavity 226), the interior pitch threads separate the pitch of the helical-shaped coil fastener 214 (as illustrated by distance X denoting the distance between the turns of the helical-shaped coil fastener 214). This in turn opens the helical-shaped coil fastener 214 to allow the pointed tip 238 of the helical-shaped coil fastener 214 to penetrate the iris tissue at a deeper, more pronounced, or normal angle.

As shown in FIG. 5D, as the helical-shaped coil fastener 214 is rotated and translated (e.g., internally translated) within the single-flange grommet 500B, the helical-shaped coil fastener 214 also rotates and translates into the iris 104. Further, as the helical-shaped coil fastener 214 exits the single-flange grommet 500B and penetrates the iris 104, the pitch of the helical-shaped coil fastener 214 changes (e.g., decreases). Thus, the helical-shaped coil fastener 214 extends into the iris 104 in an extended orientation, with at least the head 234 and/or a portion of the helical wire 236 engaging at least a portion of the internal threads of the single-flange grommet 500B to secure the single-flange grommet 500B to the iris 104, and with the haptic foot section secured between the upper flange 502B and the anterior surface of the iris 104.

Further, once the helical-shaped coil fastener 214 is in place within the iris tissue, the pitch of the spring coil returns to its natural state (as illustrated by distance <X), returning to a tighter coil with less separation between the coil pitches to create greater apposition of the IOL 212 to the iris tissue (e.g., the anterior surface thereof). Additionally, or alternatively, to achieve this self-tightening, the helical-shaped coil fastener 214 can be made from a shape memory material that changes pitch in response to body temperature or an externally applied energy source (e.g., resistive heating, applied electrical current, laser emission, etc.).

Alternatively, the directing thread pitch at the take-off or exit of the IOL 212 can place the distal tip of the helical-shaped coil fastener 214 into a more oblique angle to barely penetrate the iris tissue. Once inserted into the iris tissue, the helical-shaped coil fastener 214 would resume its natural pitch with slightly more separation between the pitches.

As another alternative (or in addition), the haptic foot section cavity could be constructed with a mechanical detent to direct the helical-shaped coil fastener pointed tip 238 posterior or downward into the iris tissue. As above, once into the iris tissue, the helical-shaped coil fastener 214 resumes its naturally pitched configuration to sweep out an area for holding the IOL 212 in place.

In another embodiment, after the helical-shaped coil fastener 214 is fully engaged with the iris tissue, the single-flange grommet 500B independently advances the helical-shaped coil fastener 214 posteriorly. In this fashion, the IOL 212 could be backed off the anterior surface of the iris 104 to a predetermined distance.

Although FIGS. 5C and 5D are illustrated with respect to the single-flange grommet 500B, the description thereof could also apply to a double-flange grommet 500A. Further, for the double-flange grommet 500A, the double-flange grommet 500A and helical-shaped coil fastener 214 could be inserted into a haptic of a tumbled and polished IOL 212 in preparation for final assembly. During the implantation process, the helical-shaped coil fastener 214 and double-flange grommet 500A could be integral and preplaced onto the haptics of the IOL. Once inserted and positioned on the iris 104 of the patient, the helical-shaped coil fasteners 214 are already preplaced and ready for insertion into the iris 104.

Figure 6:
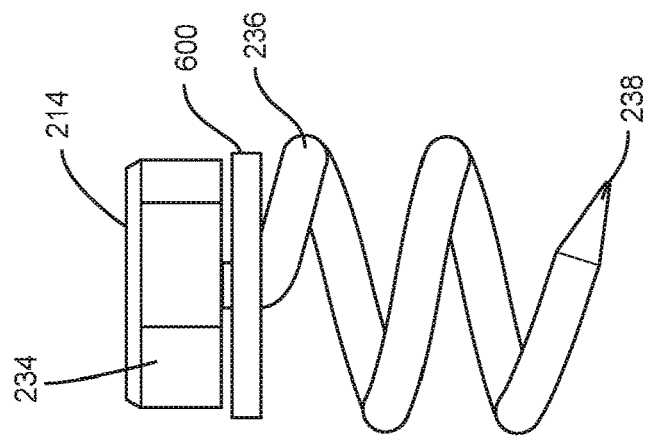
FIG. 6 is a side view of an exemplary helical-shaped coil fastener with a protective washer.

FIG. 6 is a side view of a helical-shaped coil fastener 214 with a protective washer 600 for controlling and limiting penetration depth of the helical-shaped coil fastener 214. The protective washer 600 could be used with the IOL 212 and a part of the IOL assembly 210 discussed above in FIGS. 2A-2G. The helical-shaped coil fastener 214 includes a head 234, helical wire 236, and pointed tip 238, as described above in FIGS. 2E-2G. The protective washer 600 prevents further travel of the pointed tip 238 into the iris tissue, and prevents the pointed tip 238 from penetrating or advancing too far into the depth of the iris tissue (e.g., the posterior surface of the iris tissue contains delicate musculature which would be desired to avoid). Alternatively, the depth of penetration can be limited by a mechanical detent interacting with the helical-shaped coil fastener head 234, or any location on the helical-shaped coil fastener 214, and a corresponding mechanical stop within the IOL 212, or a separate grommet in the IOL haptic foot section cavity 226.

Figure 7:
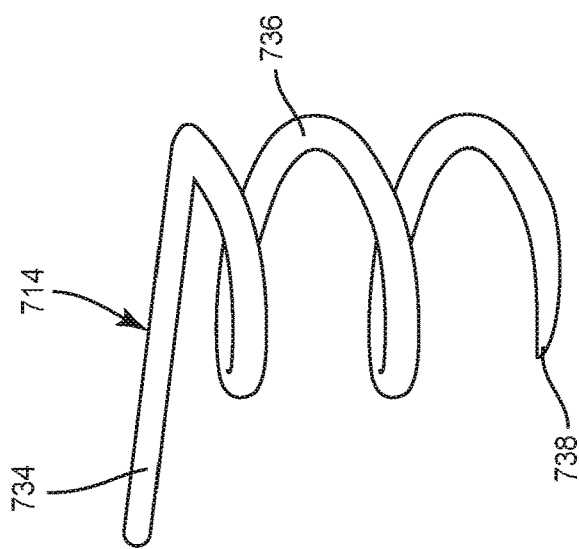
FIG. 7 is a top perspective view of another exemplary embodiment of the helical-shaped coil fastener with a head comprising a top end of a wire extending past an outer diameter of a helix of the wire.

FIG. 7 is a top perspective view of another embodiment of the helical-shaped coil fastener 714 for affixing an IOL 212 of an IOL assembly 210 to an iris 104. The helical-shaped coil fastener 714 could be used with the IOL 212 and could be a part of the IOL assembly 210 discussed above in FIGS. 2A-2G. The helical-shaped coil fastener 714 includes a head 734, helical wire 736, and pointed tip 738, as described above in FIGS. 2E-2G, except that the head 734 comprises a top end of the wire 736 that extends past an outer diameter of a helix of the wire 736. The head 734 could extend from a first side of a helix across the helix (e.g., a diameter of the helix) to and past a second side of the helix. Insertion of the helical-shaped coil fastener 714 stops when the head 734 (e.g., the top end of the wire) contacts an anterior surface of the IOL 212.

Figure 8:
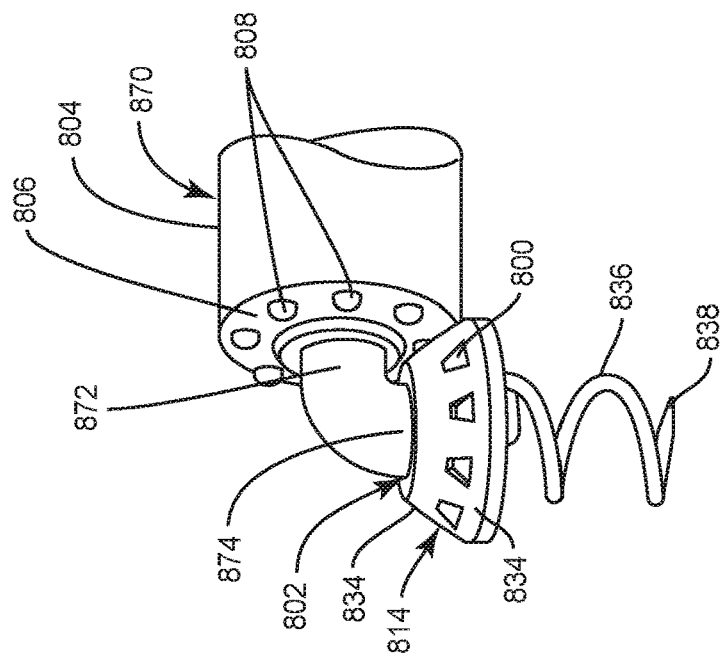
FIG. 8 is a top perspective view of another exemplary embodiment of the helical-shaped coil fastener with a head cap with circumferentially spaced mechanical notches and a fastener applicator tool engaged therewith.

FIG. 8 is a top perspective view of another embodiment of the helical-shaped coil fastener 814 for affixing an IOL 212 of an IOL assembly 210 to an iris 104. The helical-shaped coil fastener 814 could be used with the IOL 212 and could be a part of the IOL assembly 210 discussed above in FIGS. 2A-2G. The helical-shaped coil fastener 814 includes a head 834, helical wire 836, and pointed tip 838, as described above in FIGS. 2E-2G, except that the head 834 includes a plurality of circumferentially spaced notches 800 and a circular recess 802 in a top surface of the head 834. A fastener applicator tool 870 includes a first shaft 872 and a second shaft 874 perpendicular to the first shaft 872. A cylindrically-shaped axially rotatable turning mechanism 804 with a planar face 806 at an end thereof with a plurality of protrusions 880 extending from the planar face 878. The turning mechanism 804 rotates around and is axially aligned with the first shaft 872, such that the plurality of protrusions 808 are proximate the second shaft 874. In this way, when a distal end of the second shaft 874 engages the circular recess 802 of the helical-shaped coil fastener 814, at least one of the plurality of protrusions 808 engages at least one of the plurality of circumferentially spaced notches 800. Thus, as the turning mechanism 804 rotates, the plurality of protrusions 808 engage and disengage the plurality of circumferentially spaced notches 800, causing the helical-shaped coil fastener 814 to rotate about the second shaft 874 of the fastener applicator tool 870.

Figure 9:
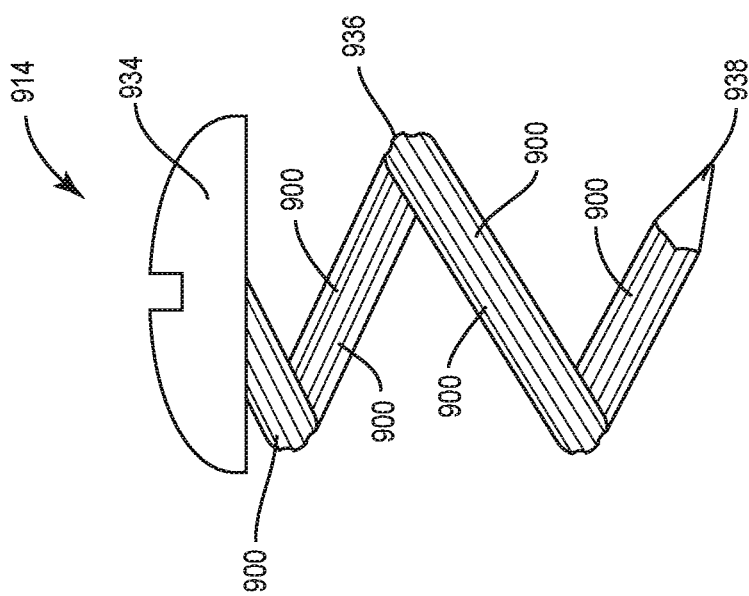
FIG. 9 is a side view of another exemplary embodiment of the helical-shaped coil fastener with a groove along a length of the wire.

FIG. 9 is a side view of another embodiment of the helical-shaped coil fastener 914 for affixing an IOL 212 of an IOL assembly to an iris 104. The helical-shaped coil fastener 914 could be used with the IOL 212 and could be a part of the IOL assembly 210 discussed above in FIGS. 2A-2E. The helical-shaped coil fastener 914 includes a head 934, helical wire 936, and pointed tip 938, as described above in FIGS. 2E-2G, except that the helical wire 936 includes one or more grooves 900 running axially along the helical wire 936. The one or more grooves 900 (e.g., ridges, lines, etc.) provide mechanical support for the helical-shaped coil fastener 914 in the iris tissue, without impacting insertion, and could be created by etching. The one or more grooves 900 could be circumferentially spaced around an axis of the helical wire 936. The one or more grooves 900 increase the surface area and contact area of the helical-shaped coil fastener 914 with the iris tissue, while reducing the cross-sectional area of insertion, and without inhibiting insertion or removal of the helical-shaped coil fastener 914 from the iris tissue. The one or more grooves 900 could be spaced for tissue interaction or where tissue could reside to improve the upward or downward stability of the IOL 212 in the iris tissue.

Figure 10:
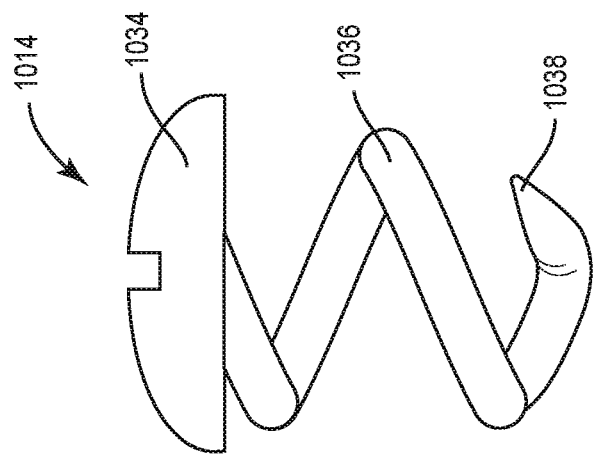
FIG. 10 is a side view of another exemplary embodiment of the helical-shaped coil fastener with an angled pointed tip.

FIG. 10 is a side view of another embodiment of the helical-shaped coil fastener 1014 for affixing an IOL 212 of an IOL assembly to an iris 104. The helical-shaped coil fastener 1014 could be used with the IOL 212 and could be a part of the IOL assembly 210 discussed above in FIGS. 2A-2G. The helical-shaped coil fastener 1014 includes a head 1034, helical wire 1036, and pointed tip 1038, as described above in FIGS. 2E-2G, except that the pointed tip 1038 is angled upward. More specifically, the helical-shaped coil fastener 1014 enters the iris tissue at an acute angle. Once screwed into iris tissue, the preformed pointed tip 1038 (and/or coil pitch) could turn the pointed tip 1038 to curve back upward toward the anterior surface of the iris (e.g., the posterior surface of the IOL 212).

Figure 11:
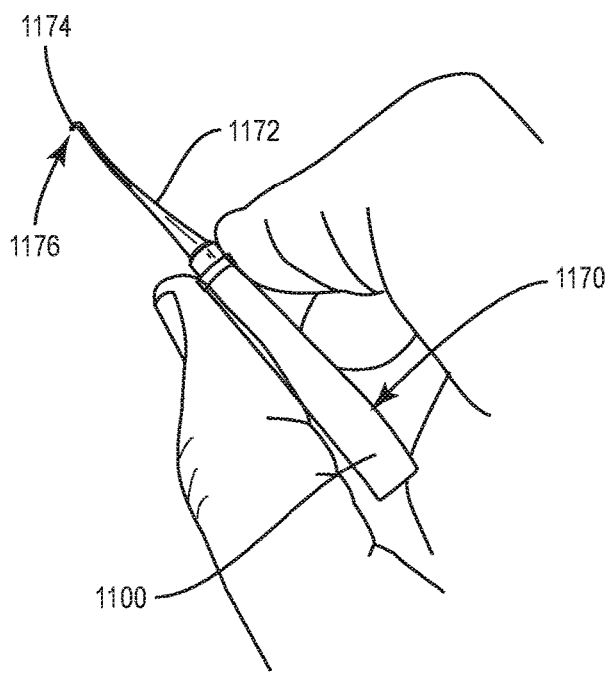
FIG. 11 is a perspective view of an exemplary digital fastener applicator tool for applying a helical-shaped coil fastener to an iris to affix an IOL to the iris.

FIG. 11 is a perspective view of a digital fastener applicator tool 1170 for applying a helical-shaped coil fastener 214 to an iris 104 to affix an IOL 212 to the iris 104. The digital fastener applicator tool 1170 could be used with any of the fasteners and/or IOL assemblies discussed above in FIGS. 2A-10. As with the fastener applicator tool of FIGS. 3C-3E, the digital fastener applicator tool 1170 includes a first cannula 1172 and a second cannula 1174 more distal than the first cannula 1172 and approximately perpendicular to the first cannula 1172. The second cannula 1174 comprises distal opening 1176. Distal opening 1176 can be round or circular in shape at the distal end opening, but other shapes that include non-round and/or straight edges, like a polygonal-shaped opening, such as a hexagonal-shaped opening for example, is possible. For a hexagonal-shaped distal end opening, the haptic hole or anterior surface of the grommet would have a similar non-round shape such as a hexagonal shape for mating or engaging the digital fastener applicator tool distal end opening to the haptic hole. The mating of the non-round shapes or polygonal shapes would further stabilize the haptic and lens when the helical coil was being screwed into place into the iris tissue. Further, the digital fastener applicator tool 1170 includes a handle portion 1100 extending from a proximal end of the first cannula 1172. The digital fastener applicator tool 1170 includes a digital button to actuate operation of the digital fastener applicator tool 1170, such as to turn a helical-shaped coil fastener 214 at least partially contained within the distal opening 1176. As shown, the handle portion 1100 is configured to be positioned and compressed between a thumb and finger (e.g., where further compressing a button actuates the digital fastener applicator tool 1170).

The digital fastener applicator tool 1170 could include a feedback of force sensing mechanism. The force sensing mechanism could be designed with a torque meter to provide feedback to the surgeon for when the helical-shaped coil fastener 214 is engaged or tightened into iris tissue. The force sensing mechanism could also have indicia that provides external feedback to the surgeon. The force sensing mechanism could also be tied to an audible tone or signal for the physician indicating when the rotation of the helical-shaped coil fastener 214 is complete or within specification. Alternatively, the digital fastener applicator tool 1170 could be limited to only a certain number of rotations that serve to limit the amount of penetration of the helical-shaped coil fastener 214 into the iris tissue.

Figure 12:
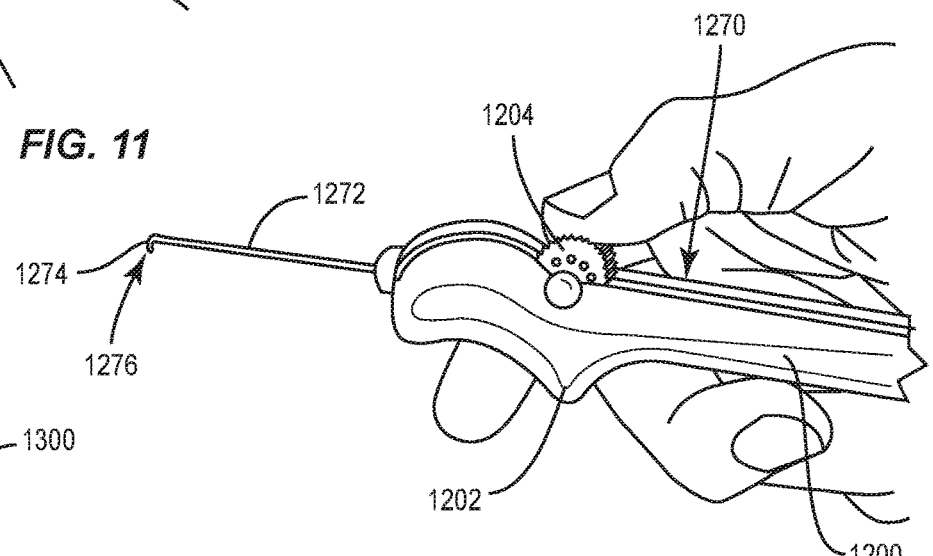
FIG. 12 is a perspective view of an exemplary mechanical fastener applicator tool for applying a helical-shaped coil fastener to an iris to affix an IOL to the iris.

FIG. 12 is a perspective view of a mechanical fastener applicator tool 1270 for applying a helical-shaped coil fastener 214 to an iris 104 to affix an IOL 212 to the iris 104. The digital fastener applicator tool 1270 could be used with any of the fasteners and/or IOL assemblies discussed above in FIGS. 2A-10. As with the fastener applicator tool of FIGS. 3C-3E and FIG. 11, the mechanical fastener applicator tool 1270 includes a first cannula 1272 and a second cannula 1274 more distal than the first cannula 1272 and approximately perpendicular to the first cannula 1272. The second cannula 1274 comprises distal opening 1276. Further, the mechanical fastener applicator tool 1270 includes a handle portion 1200 extending from a proximal end of the first cannula 1272. A bottom surface of the handle portion 1200 includes ergonomic contours 1202 (e.g., notches, grips, knurls, etc.) for handling by a surgeon (e.g., for engaging the finger tips, palm, or thumb of the physician). The top surface of the handle portion 1200 includes a mechanical actuator 1204 (e.g., a wheel) for manual rotation by a surgeon's finger or thumb. Rotation of the mechanical actuator 1204 could actuate operation of the digital fastener applicator tool 1270, such as to turn a helical-shaped coil fastener 214 at least partially contained within the distal opening 1276. Manually rotating the mechanical actuator 1204 operates a cable that in turn rotates a driver to screw the helical-shaped coil fastener 214 into the iris 104. Further, the handle portion 1200 could include indicia or other indicators for the number of rotations made by the helical-shaped coil fastener 214. This can be measured by the greater the number of coils of the helical-shaped coil fastener 214 inserted into the iris tissue, the greater the apposition in the iris tissue.

The descriptions and features of the handle portions 1100, 1200 of the digital fastener applicator tool 1170 and the mechanical fastener applicator tool 1270 could be interchangeable. For both the digital fastener applicator tool 1170 and the mechanical fastener applicator tool 1270, the handle portions 1100, 1200 are symmetrical about a central axis (e.g., for right and left handed positions. The handle portions 1100, 1200 are balanced, lightweight, configured to fit in a hand and be manipulated by fingers, and could include an elongated distal portion with a low profile for working with a small diameter space. The fact that the handle portions 1100, 1200 are balanced and easily gripped by the physician facilitates control of the location of the distal openings 1176, 1276 within the anterior chamber 110 of the eye 100. The handle portions 1100, 1200 could also be disposable or reusable. The actuators of the fastener applicator tools 1170, 1270 are configured to rotate and/or translate the helical-shaped coil fastener 214 into the iris 104.

Figure 13:
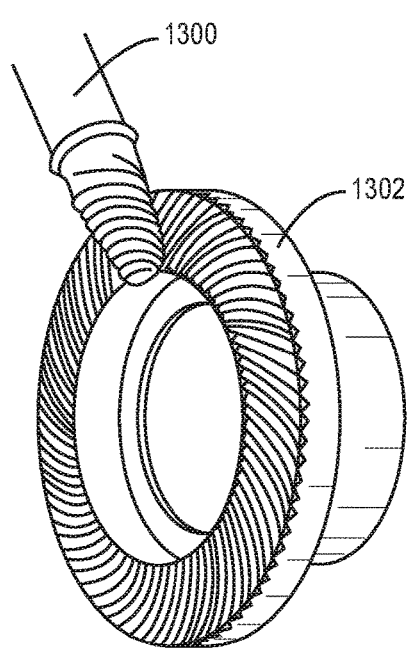
FIG. 13 is a perspective view of an exemplary rotational cam and mandrel which could be used in the fastener applicator tool of FIGS. 11 and/or 12.

FIG. 13 is a perspective view of a mandrel 1300 and rotational cam 1302 which could be used in the fastener applicator tools 1170, 1270 of FIGS. 11 and/or 12 to rotate and/or translate one or more helical-shaped coil fasteners 214 through the fastener applicator tools 1170, 1270. The rotational cam 1302 and mandrel 1300 could be used with any of the fasteners and/or IOL assemblies discussed above in FIGS. 2A-10 and/or the fastener applicator tools 1170, 1270. In particular, the rotational mandrel 1300 defines a central aperture where one or more helical-shaped coil fasteners 214 can pass through. Further, the rotational cam 1302 and mandrel 1300 can be used with respect to the perpendicular orientation of the first cannula 1172, 1272 relative to the second cannula 1174, 1274. The rotation of the mandrel 1300 can be accomplished by one or more cams 1302 that mechanically engage to rotate the distal end of the fastener applicator tool 1170, 1270.

Figure 14A:
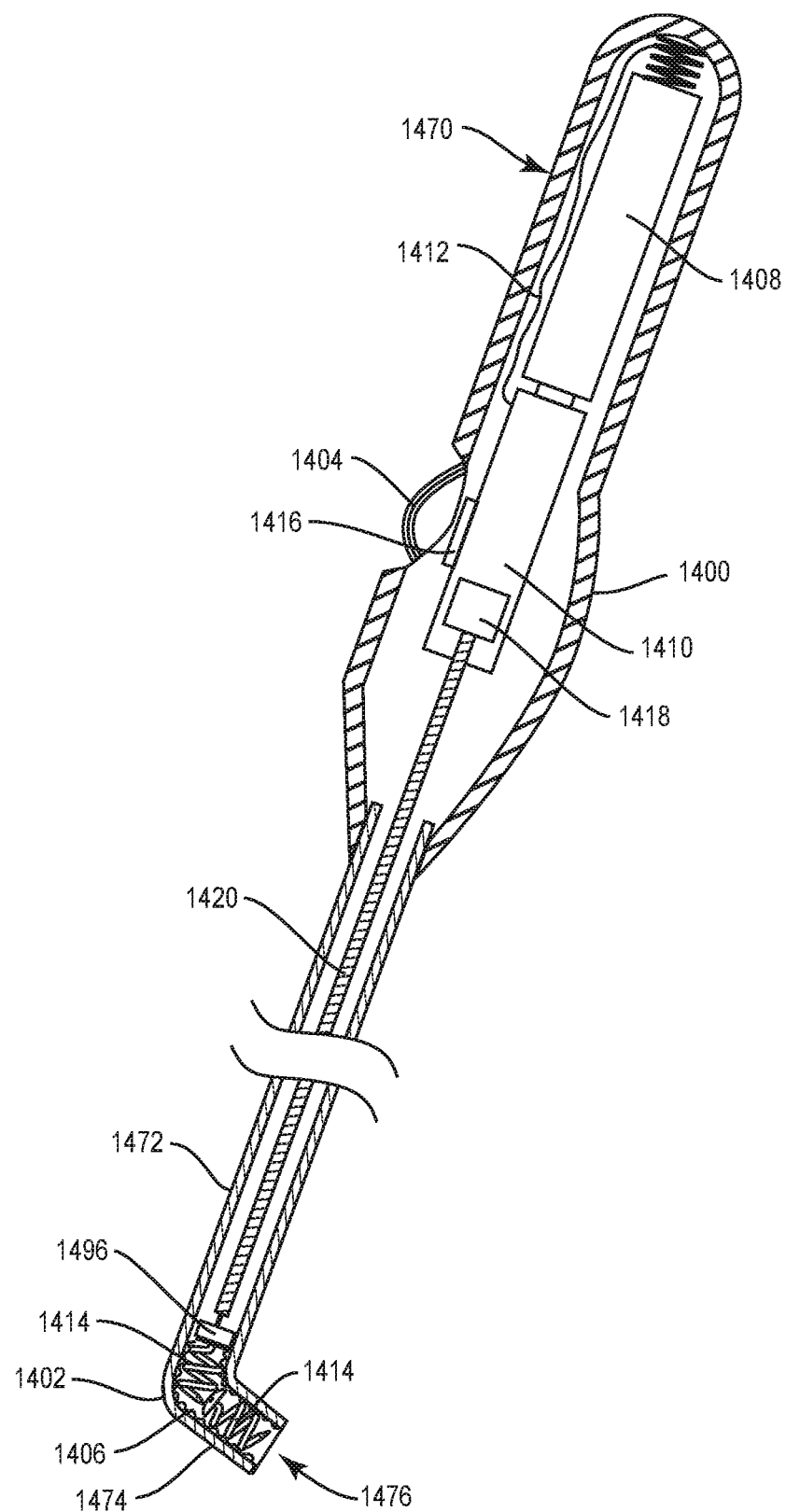
FIG. 14A is a cross-sectional view of a digital fastener applicator tool for applying a helical-shaped coil fastener to an iris to affix an IOL to the iris.
Figure 14B:
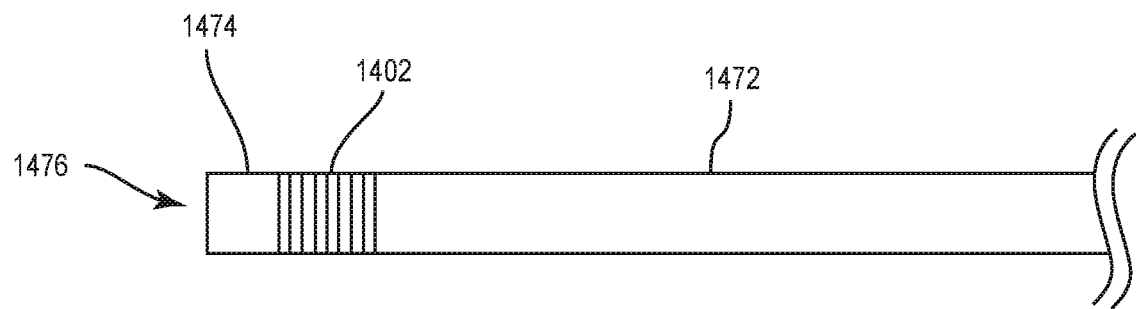
FIG. 14B is a side view illustrating a distal end of the cannula of the digital fastener applicator tool of FIG. 14A in a straight orientation.
Figure 14C:
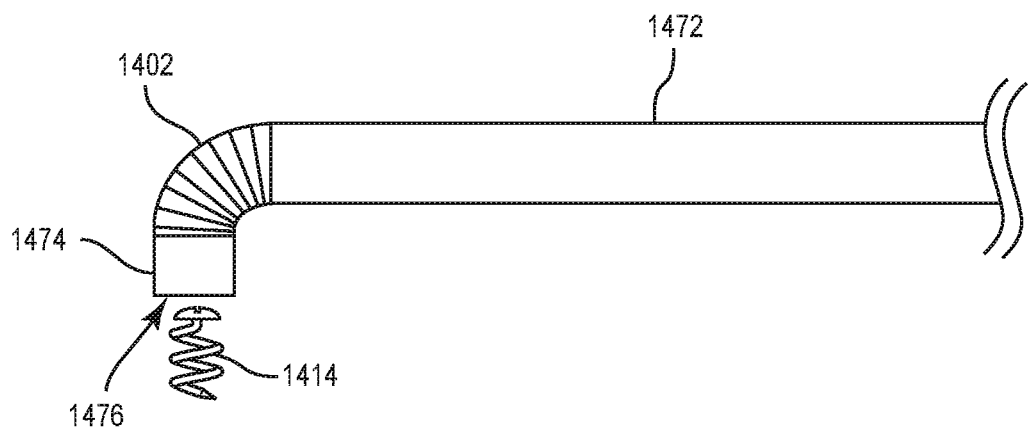
FIG. 14C is a side view illustrating a distal end of the cannula of the digital fastener applicator tool of FIG. 14A in a bent orientation.

FIGS. 14A-14C are views of a digital fastener applicator tool 1470 for applying a helical-shaped coil fastener 214 to an iris 104 to affix an IOL 212 to the iris 104. The digital fastener applicator tool 1470 could be used with any of the fasteners and/or IOL assemblies discussed above in FIGS. 2A-10 and/or could include one or more features discussed with respect to the fastener applicator tools 1170, 1270 of FIGS. 11 and 12 and/or the rotational cam 1302 and mandrel 1300 of FIG. 13. Although a digital fastener applicator tool 1470 is discussed, the features described could also apply to a mechanical fastener applicator tool. As with the fastener applicator tool discussed above in FIGS. 11 and 12, the digital fastener applicator tool 1470 includes a first cannula 1472 and a second cannula 1474 more distal than the first cannula 1472 and approximately perpendicular (or angled relative to) to the first cannula 1472 at bend portion 1402. As discussed above, the angled orientation of the first cannula 1472 and second cannula 1474 allows the distal end of the digital fastener applicator tool 1470 to be inserted through an incision 300 in the eye 100 and then rotated to place a distal opening 1476 in the second cannula 1474 into engagement with an IOL haptic 218. The first cannula 1472 and/or second cannula 1474 could include internal threads 1406 (or other bumps, ridges, and/or threads to guide one or more helical-shaped coil fasteners 1414 through and out of the digital fastener applicator tool 1470.

Helical-shaped coil fasteners 1414 could be preloaded into a handle portion 1400, the first cannula 1472, or the second cannula 1474. Thus, for example, two or more helical-shaped coil fasteners 1414 could be preloaded for each haptic 218 and/or each IOL 212. The helical-shaped coil fasteners 1414 could be loaded into the digital fastener applicator tool 1470 by the surgeon at the time of use. Alternatively, the helical-shaped coil fasteners 1414 could be picked up by a distal end of the digital fastener applicator tool 1470 (e.g., by a driver 1496 through the distal opening 1476. For some helical-shaped coil fastener 1414 configurations, it may be advantageous to require the physician to load the coil onto the instrument.

For helical-shaped coil fasteners 1414 made from a shape memory material (e.g., nitinol), reducing the amount of time for the coil to be in a stressed state while undergoing sterilization, shipping, and shelf life may improve the overall fatigue and durability life of the helical-shaped coil fastener 1414.

Further, the digital fastener applicator tool 1470 includes a handle portion 1400 extending from a proximal end of the first cannula 1472. The top surface of the handle portion 1400 includes a digital actuator 1404 (e.g., a finger button) with easy access to the digital actuator 1404. The bottom surface of the handle portion 1400 could be contoured (e.g., contain grips) for gripping and handling of the digital fastener applicator tool 1470.

At a proximal end of the handle portion 1400 is a battery 1408 in mechanical and electrical connection with a motor 1410 (e.g., via connecting wire 1412), such as at a proximal end of the motor 1410. The battery 1408 could be rechargeable through a port in the handle portion 1400. A motor switch 1416 of the motor 1410 is proximate the digital actuator 1404, such that pressing on the digital actuator 1404 activates the motor switch 1416 to activate the motor 1410.

A distal end of the motor 1410 includes a drive cylinder 1418, where operation of the motor 1410 rotates the drive cylinder 1418. The drive cylinder 1418 is mechanically connected (e.g., mechanically coupled) to a rotating cable 1420 at a proximal end thereof. A distal end of the rotating cable 1420 includes the driver 1496. The rotating cable 1420 extends into, and is extendable/retractable through, the first cannula 1472 and the second cannula 1474 beyond the handle portion 1400. In other words, the rotating cable 1420 can telescope and/or stretch to maintain physical connection between the driver 1496 and the motor 1410 as the driver 1496 translates through the first cannula 1472 and/or second cannula 1474.

As shown in FIG. 14A, the driver 1496 is physically connected to one of a plurality of helical-shaped coil fasteners 1414 (e.g., by magnetic connection, physical engagement, etc.) that are positioned within the first cannula 1472 and second cannula 1474. The two helical-shaped coil fasteners 1414 are adjacent to one another (e.g., immediately behind one another). When a user (e.g., physician, surgeon, etc.) depresses the digital actuator 1404, the digital actuator 1404 activates the motor switch 1416 which activates the motor 1410. The motor 1410 then rotates the drive cylinder 1418, which rotates the rotating cable 1420, which rotates the driver 1496. As the driver 1496 rotates, the driver translates through the first cannula 1472 and/or second cannula 1474 by the internal threads 1406. As the driver 1496 rotates and/or translates through the first cannula 1472 and/or second cannula 1474, the driver 1496 rotates and/or translates one or more the helical-shaped coil fasteners 1414 connected (e.g., mechanically engaged) with the driver 1496, which provides rotational energy to the helical-shaped coil fastener 1414). In this way, rotating a first helical-shaped coil fastener 1414 connected to the driver 1496 could in turn rotate a second helical-shaped coil fastener 1414 in mechanical communication with the first helical-shaped coil fastener 1414. The driver 1496 rotates and/or translates the helical-shaped coil fastener 1414 until at least a portion of one of the helical-shaped coil fasteners 1414 exits the digital fastener applicator tool 1470. Once the helical-shaped coil fastener 1414 is inserted into the iris tissue, the driver 1496 detaches from the helical-shaped coil fastener 1414. Alternatively, or additionally, the distal end of the fastener applicator tool 1470 contains an engaging and turning mechanism for mating with the helical-shaped coil fastener 1414.

FIG. 14B is a side view illustrating a distal end of the second cannula 1474 of the digital fastener applicator tool 1470 of FIG. 14A in a straight orientation. As shown, the second cannula 1474 is axially aligned with the first cannula 1472 forming a linear angle relative to one another. This could lower the insertion profile of the second cannula 1474 into the eye 100.

FIG. 14C is a side view illustrating a distal end of the second cannula 1474 of the digital fastener applicator tool 1470 of FIG. 14A in a bent orientation forming a non-linear angle relative to one another. Once inserted into the eye 100, the second cannula 1474 could be bent along bend portion 1402 such that the second cannula 1474 is perpendicular or angled relative to the first cannula 1472. This facilitates use of the digital fastener applicator tool 1470 by a surgeon. Articulation of the distal tip of the digital fastener applicator tool 1470 could be done by pulling or twisting an outer sleeve connected to a bendable section of the distal end. In this way, the distal end of the digital fastener applicator tool 1470 could be moveable, but alternatively, the distal end could be fixed and shaped to an angled bend (e.g., 45 degrees, 90 degrees, etc.).

Figure 15:
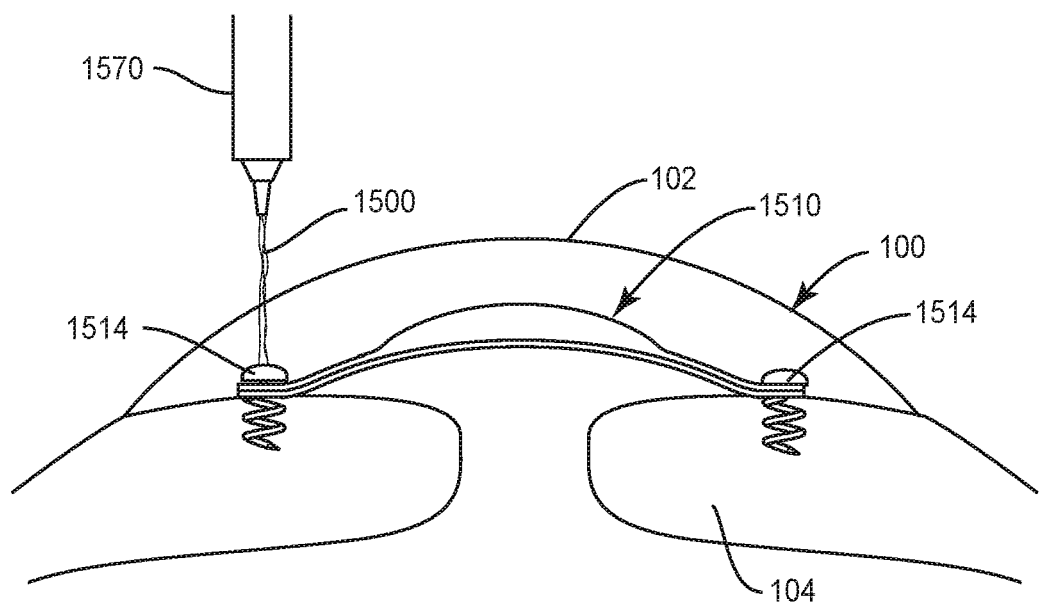
FIG. 15 is a cross-sectional side view of an exemplary applicator tool affixing a fastener and/or anchor from outside the eye by an external heat source.

FIG. 15 is a cross-sectional side view of a digital fastener applicator tool 1570 affixing a helical-shaped coil fastener 1514 (or any other type of fastener and/or anchor) from outside the eye 100 by an external heat source. More specifically, if the helical-shaped coil fastener 1514 is made of a heat changing material (e.g., nitinol), then from outside the eye 100, the fastener applicator tool 1570 emits a laser 1500 (or other heat source or electrical probe) through the cornea 102 to heat the helical-shaped coil fastener 1514 from outside the eye 100. The applied heat causes the helical-shaped coil fastener 1514 to rotate and/or penetrate the iris 104. Alternatively, a heat source could be applied by direct contact with an instrument.

Alternatively, or additionally, the heat changing material could react and change shape upon the application of a known amount of thermal exposure (e.g., body temperature), an electric current (e.g., from the body), and/or to a higher temperature or electric current supplied from an instrument and/or the fastener applicator tool 1570. Once exposed to the higher temperature or electrical current, a nitinol form can change shape or be made to uncoil or turn. In this instance, the helical-shaped coil fastener 1514 would rotate to screw into the iris 104 without any applied external mechanical force and the rotational energy would be supplied by the coil material itself.

As another embodiment, the helical-shaped coil fastener 1514 can be supplied with a stored energy or spring action that is released once the IOL 212 is positioned onto the iris 104. The helical-shaped coil fastener 1514 would screw into the iris 104 by the rotational force supplied by a known and pre-determined spring action of the coil material. The mechanical release would supply the rotational force to the screwing action.

Alternatively, the helical-shaped coil fastener 1514 can be made from a ferromagnetic material that can react to a supplied magnetic field or magnetic source. In this instance, the exposure to the magnetic field would cause the coil to rotate and screw into the iris. Advantageously, the magnetic field can be supplied from either a location immediately adjacent to the IOL 212 (e.g., supplied by an instrument within the eye) or from an applied magnetic field on the exterior of the eye, and can be made to react with the ferromagnetic coil material.

Attachment of the IOL 212 to the iris 104 can also be accomplished through an intraocular suturing system. The suturing system would provide a curved needle to pierce the iris 104 and transport a suture through the iris 104 and onto the IOL 212. Once pulled through a locking loop, excess suture can be cut and removed.

Figure 16A:
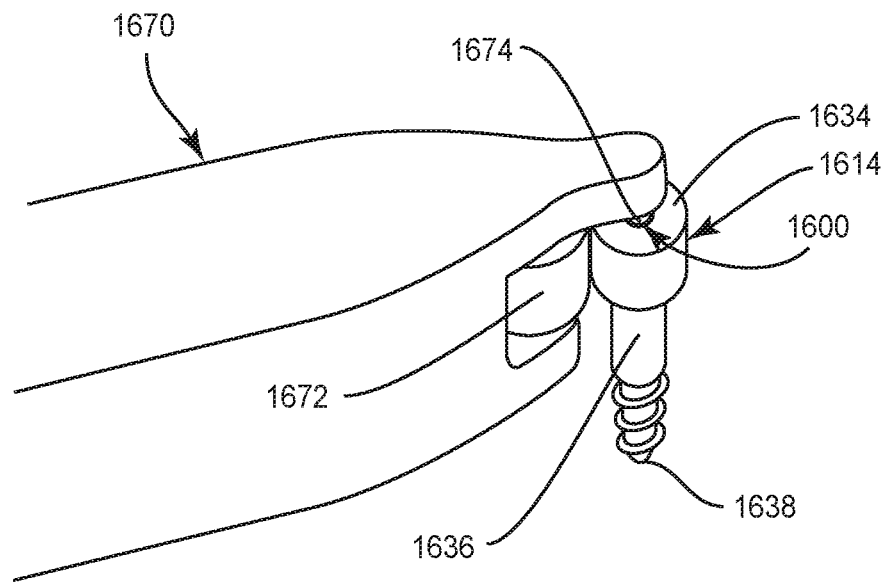
FIG. 16A is a top perspective view of another exemplary embodiment of the intraocular implant assembly using a fastener applicator tool with a friction drive wheel engaging a screw fastener to attach an IOL to an iris.
Figure 16B:
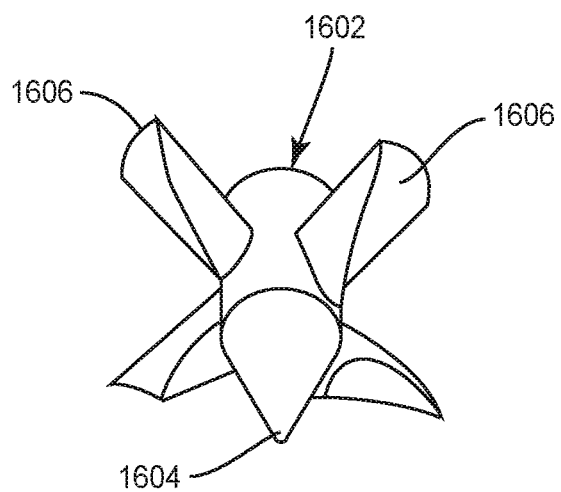
FIG. 16B is a bottom perspective view of the anchor for use with the screw fastener of FIG. 16A in an open orientation.
Figure 16C:
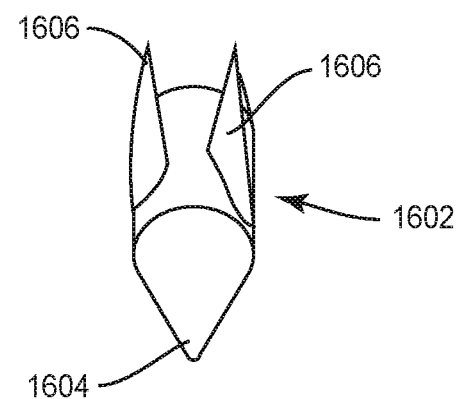
FIG. 16C is a bottom perspective view of the anchor of FIG. 16B in a closed orientation.

FIGS. 16A-16C are views of another embodiment of the intraocular implant assembly utilizing anchors for affixing an IOL 212 of an IOL assembly 210 to an iris 104. Shown in FIG. 16A is an intraocular implant assembly IOL haptic foot section, along with a screw fastener 1614 and applicator tool 1670. The screw fastener 1614 could be used with any of the IOL assemblies discussed above in FIGS. 2A-2G. As shown, the screw fastener 1614 includes a cylindrical head 1634 with an engagement hole 1600 at a top surface of the cylindrical head 1634, and a threaded shaft 1636 with a pointed tip 1638. The applicator tool 1670 includes a friction driver wheel 1672 extending from a distal end of the applicator tool 1670. The applicator tool 1670 also includes a protrusion 1674 proximate to and positioned more distally than the friction driver wheel 1672. The protrusion 1674 is sized and shaped to engage the screw fastener engagement hole 1600. The protrusion 1674 and the friction driver wheel 1672 are spaced apart such that when the protrusion 1674 engages the screw fastener engagement hole 1600, the friction driver wheel 1672 contacts the outer surface of the screw fastener cylindrical head 1634. Accordingly, when the friction driver wheel 1672 rotates in a first direction, the cylindrical head 1634 rotates in a second direction opposite to the first direction about the engagement hole 1600. During insertion of the screw fastener 1614, the applicator tool protrusion 1674 stabilizes the screw fastener 1614, provides a rotation point for the screw fastener 1614, and ensures contact of the screw fastener head 1634 with the friction driver wheel 1672.

FIGS. 16B and 16C are views of an anchor for use with the screw fastener 1614 of FIG. 16A. An anchor 1602 (e.g., similar to a sheet rock anchor or a molly bolt anchor) could be used to attach the IOL 212 once it is inserted into the eye, where the IOL 212 then uses the anchor 1602 to easily attach the IOL 212 to the iris 104. The anchor 1602 could be used with any of the IOL assemblies discussed above in FIGS. 2A-2G.

FIG. 16B is a perspective view of an anchor 1602 in an open orientation, which could be used with the screw fastener 1614. The anchor 1602 includes a pointed tip 1604 and one or more circumferentially spaced wings 1606, each wing 1606 includes a stabilizing feature on a bottom surface thereof to engage the anterior surface of the iris 104. The anchor 1602 helps orient the screw fastener 1614 pointed tip 1638 and decreases the amount of axial force required for the screw fastener 1614 to penetrate the iris 104. In this way, the stabilizing feature of the wings 1606 prevents axial rotation of the anchor 1602.

FIG. 16C is a perspective view of the anchor 1602 of FIG. 16B in a closed orientation, after the screw fastener 1614 has penetrated the anchor 1602 and the iris 104. In this way, the wings 1606 of the anchor 1602 fold upward as the anchor 1602 and the screw fastener 1614 are inserted into the iris 104. The wings 1606 of the anchor 1602 could be biased towards the open orientation for increased stability and security within the iris 104. The anchor 1602 could block light, and could remain within the iris 104 if the screw fastener 1614 is removed.

Alternatively, the anchor 1602 could be inserted in the closed orientation first, such that the screw fastener 1614 and anchor 1602 penetrate the iris with the anchor 1602 in a closed orientation. Once inserted, the anchor 1602 then changes to the open orientation, thereby securing the anchor 1602 and screw fastener 1614 (mechanically attached to the anchor 1602) within the iris 104. Either way, the anchor 1602 could be activated to change from a closed orientation to an open orientation (and/or vice versa) through the use of a screw and/or push pull mechanism.

Figure 17:
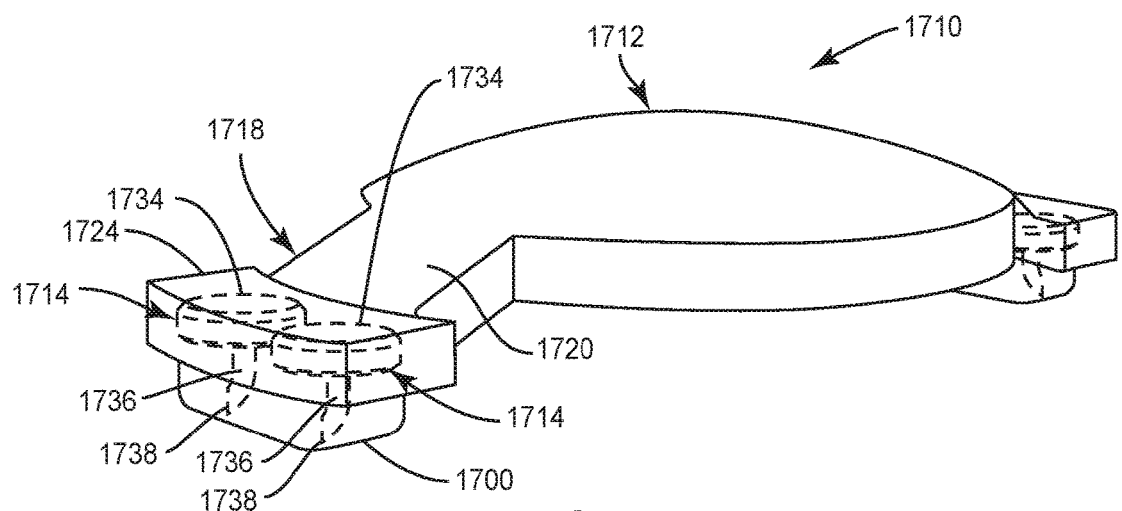
FIG. 17 is a perspective view of an exemplary IOL assembly with integrated tack fasteners.

FIG. 17 is a perspective view of an IOL assembly 1710 with integrated tack fasteners 1714 for affixing an IOL assembly 1710 to the iris 104. An IOL assembly 1710 includes all of the components discussed with respect to FIGS. 2A-3E above, except that each haptic 1718 of an IOL 1712 includes a single riser section 1720, and a haptic foot section 1724 includes integrated tacks 1714 (e.g., pins), instead of a helical-shaped coil fastener. Each integrated tack 1714 includes a head 1734 and a shaft 1736 with a pointed tip 1738. The pointed tip 1738 could be bent relative to the shaft 1736 for ease of penetration. More specifically, the head 1734 of each tack 1714 is within the haptic foot section 1724 with a portion of the shaft 1736 and the pointed tip 1738 protruding from a bottom surface of the haptic foot section 1724. Prior to insertion, a protective cover 1700 is attached to the underside of the haptic foot section 1724 to enclose the pointed tips 1738 of the tacks 1714 to prevent accidental damage to the IOL 1712 and/or iris 104 during folding and insertion and/or removal. More specifically, the cover 1700 could be removed with a tool once the IOL 1712 is in place and properly positioned, thereby exposing the tack pointed tips 1738. This could be a two handed technique, one to hold the IOL 1712 and one to remove the cover 1700. The IOL 1712 could then be pushed down with a paddle to secure the IOL relative to the iris 104. A removal tool could also be required to include a cover to remove the IOL 1712 from the eye 100 to protect the iris 104 from the tacks 1714.

Figure 18:
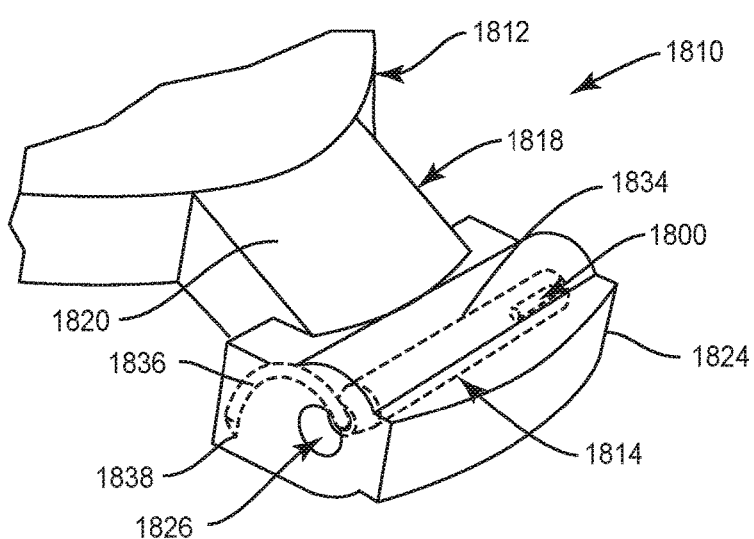
FIG. 18 is a perspective view of an enclosed channel within a haptic foot section of an IOL assembly with a perpendicular hook fastener positioned within the haptic foot section.

FIG. 18 is a perspective view of an enclosed channel within a haptic foot section 1824 of an IOL assembly with a perpendicular hook fastener positioned within the haptic foot section for affixing an IOL assembly 1710 to the iris 104. An IOL assembly 1810 includes all of the components discussed with respect to FIGS. 2A-3E above, except that each haptic 1818 of an IOL 1812 includes a single riser section 1820, and a haptic foot section 1824 is hollowed to define an enclosed channel 1826 with a perpendicular hook fastener 1814 positioned therein, instead of using a helical-shaped coil fastener. More specifically, the haptic foot section 1824 defines the enclosed channel 1826 perpendicular to the haptic riser section 1820. The perpendicular hook fastener 1814 includes a shaft 1834 with a female thread 1800 at a first end, and a hook 1836 with a pointed tip 1838 at a second end (opposite to the first end). The hook 1836 is oriented perpendicular to the shaft 1834 such that rotation about an axis of the shaft 1834 engages the hook 1836 with the anterior surface of the iris 104, thereby securing the IOL 1812 to the iris 104. The perpendicular hook fastener 1814 could be preloaded in the haptic foot section enclosed channel 1826, with the perpendicular hook fastener 1814 pointed tip 1838 safely positioned within the haptic foot section 1824. An insertion tool can then be threaded and inserted into the female thread 1800 of the perpendicular hook fastener 1814 to engage the perpendicular hook fastener 1814 and rotate it about an axis. The rotation force pushes the hook fastener pointed tip 1838 through the bottom surface of the haptic foot section 1824 and into the iris 104 (or the IOL 1812 could be squeezed to break the hook 1836 free from the haptic foot section 1824). Alternatively, the female thread 1800 could instead be geometrically shaped to receive a correspondingly shaped insertion tool. For example, the perpendicular hook fastener 1814 could include a keyed or hexagonal channel to receive a correspondingly shaped insertion tool.

Figure 19:
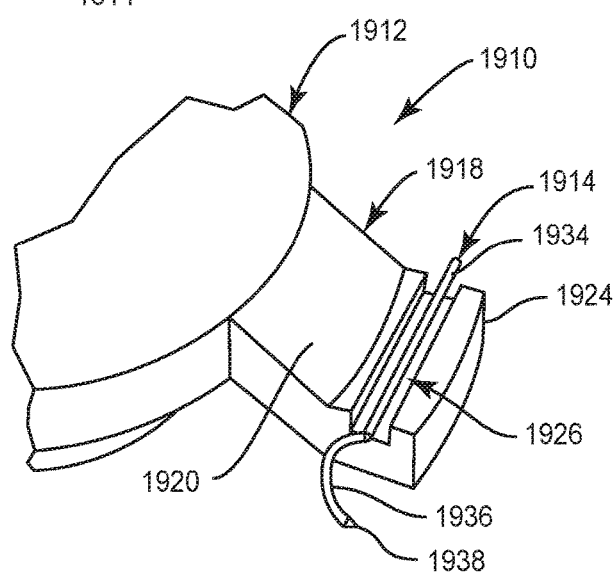
FIG. 19 is a perspective view of an open channel in a haptic foot section of an IOL assembly with a perpendicular hook fastener positioned within the open channel.

FIG. 19 is a perspective view of an open channel 1926 in a haptic foot section 1924 of an IOL assembly 1910 with a perpendicular hook fastener 1914 positioned within the open channel 1926 for attaching an IOL 1912 to an iris 104. The IOL assembly 1910 includes all of the components discussed with respect to FIGS. 2A-3E above, except that each haptic 1918 of an IOL 1912 includes a haptic riser section 1920, and a haptic foot section 1924 defines an open channel 1926 and a rotational hook fastener 1914 positioned therein, instead of a helical-shaped coil fastener. The open channel 1926 is perpendicular to the haptic riser section 1920, but has an opened top. The rotational hook fastener 1914 includes a shaft 1934 with a perpendicular hook 1936 extending from one end, the perpendicular hook including a pointed tip 1938. Accordingly, the rotational hook fastener 1914 can be placed in the open channel 1926, and once positioned in the open channel 1926, the rotational hook fastener 1914 can be rotated so that the pointed tip 1938 penetrates and engages the iris 104, thereby securing the IOL 1912 to the iris 104.

Figure 20:
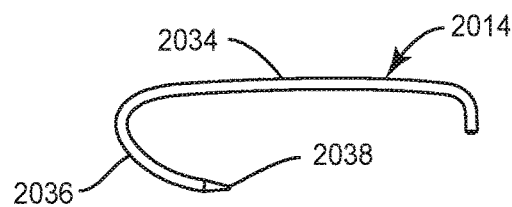
FIG. 20 is a side view of an exemplary fishhook fastener to engage a haptic and penetrate an anterior surface of an iris to affix an IOL to the iris.

FIG. 20 is a side view of a fishhook fastener for attaching an IOL 2012 to an iris 104. An IOL assembly includes all of the components discussed with respect to FIGS. 2A-3E and FIG. 19 above, including that a haptic foot section 2024 includes an open channel 2025, except for the inclusion of a fish hook fastener 2014, instead of a helical-shaped coil fastener. The fish hook fastener 2014 is inserted into the iris 104 such that a pointed tip 2038 of a hook 2036 penetrates the iris 104, and a shaft 2034 of the fish hook fastener 2014 compresses against an open channel 2025, thereby securing an IOL 2012 to the iris 104. More specifically, the fish hook fastener 2014 penetrates the iris 104, and the shaft 2034 is then rotated about the hook 2036 to its final position.

Figure 21A:
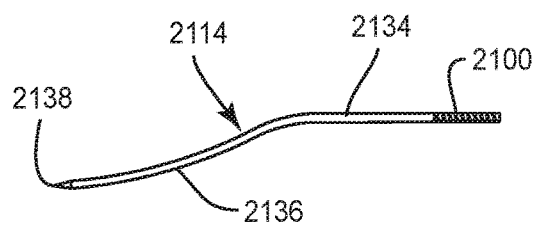
FIG. 21A is a side view of an exemplary pushpin fastener to engage a haptic and penetrate an anterior surface of an iris to affix an IOL to the iris.

FIG. 21A is a side view of a pushpin fastener 2114 for attaching an IOL 1912 to an iris 104. An IOL assembly includes all of the components discussed with respect to FIGS. 2A-3E and FIG. 19 above, including that a haptic foot section 2124 includes an open channel 2125, except for the inclusion of a pushpin fastener 2114. The pushpin fastener 2114 includes a pointed tip 2138 at a first end and an external threaded end 2100 (opposite the first end). The pushpin fastener 2114 has a straight portion 2134 (proximate the external threaded end 2100), and a curved portion 2136 proximate the pointed tip 2138. The straight portion 2134 is angled relative to the curved portion 2136. The threaded end 2100 can be used for both insertion and removal.

Figure 21B:
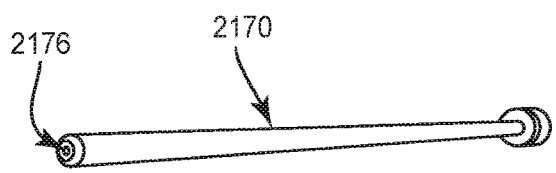
FIG. 21B is a perspective view of a fastener applicator tool for affixing the pushpin fastener of FIG. 21A.

FIG. 21B is a perspective view of a fastener applicator tool 2170 for affixing the pushpin fastener 2114 of FIG. 21A. The fastener applicator tool 2170 includes an internally threaded end 2176 to engage the threaded end 2100 of the pushpin fastener 2114. The applicator tool 2170 can be used to insert and rotate the pushpin fastener 2114 to penetrate the iris tissue and secure the pointed tip 2138 of the pushpin fastener 2114 within the iris 104. The pushpin fastener 2114 straight portion 2134 is then positioned within an open channel 2125 and an IOL 2112 is secured to the iris 104. The threaded end 2100 could extend past an end of the open channel 2125 so that the threaded end 2100 is accessible to the fastener applicator tool 2170 for removal.

Figure 22A:
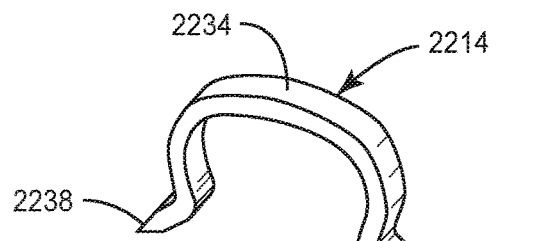
FIG. 22A is a perspective view of an spring clip fastener to engage a haptic and penetrate an anterior surface of an iris to affix an IOL to the iris.

FIG. 22A is a perspective view of a spring clip fastener 2214 for attaching an IOL to an iris 104. A spring clip fastener 2214 includes a general U-shaped clip 2234 with a first pointed tip 2238 extending outwardly from a first end and a second pointed tip 2238 extending outwardly from a second end (opposite the first end). The first and second pointed tips 2238 extend away from each other. In this way the spring clip fastener 2214 can be pinched (bringing the first and second pointed tips 2238 closer to one another), and inserted into the iris 104 while pinched. Releasing the spring clip fastener 2214 in location next to the iris 104 helps push the spring clip fastener 2214 into the iris 104.

Figure 22B:
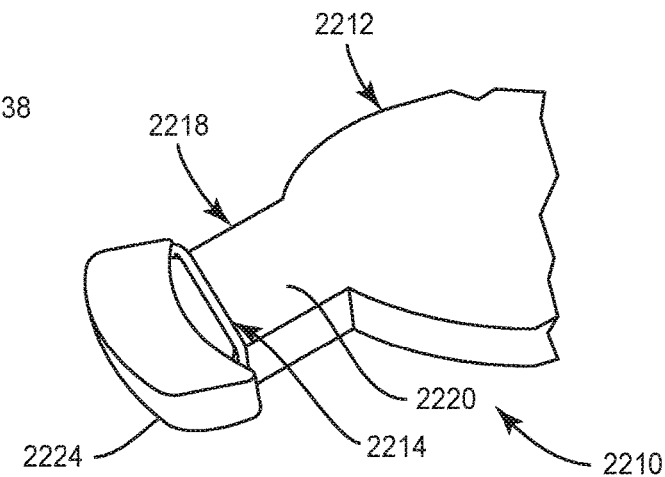
FIG. 22B is a perspective view of the spring clip fastener of FIG. 22A positioned over an IOL haptic riser section, an enlarged foot section preventing disengagement of the IOL from the spring clip.

FIG. 22B is a perspective view of the spring clip fastener 2214 of FIG. 22A positioned over an IOL haptic riser section 2220 of a haptic 2218 of an IOL 2212 of an intraocular implant assembly 2210, an enlarged foot section 2224 (wider than the haptic riser section 2220) prevents disengagement of the IOL 2212 from the spring clip fastener 2214. The haptic foot section 2224 can be pushed through the spring clip fastener 2214, after the spring clip fastener 2214 has been positioned in the iris 104. Alternatively, the spring clip fastener 2214 could be applied after the IOL 2212 has been positioned on the iris 104.

Figure 23A:
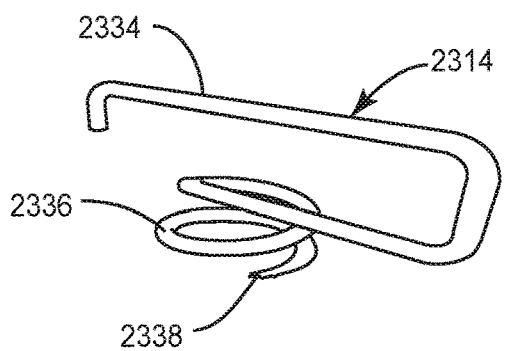
FIG. 23A is a perspective view of a helical-shaped coil fastener with a rectangular-shaped wire loop head.

FIG. 23A is a perspective view of a helical-shaped coil fastener 2314 with a rectangular-shaped wire loop head 2334 for attaching an IOL 2212 to an iris 104. An IOL assembly includes all of the components discussed with respect to FIGS. 2A-3E and FIG. 22B above, including an enlarged haptic foot section 2224, except for the inclusion of a helical-shaped coil fastener 2314. The helical-shaped coil fastener 2314 includes a helical wire 2336 with a pointed tip 2238, and the rectangular-shaped wire loop head 2334 extends from a top of the helical wire 2336.

Figure 23B:
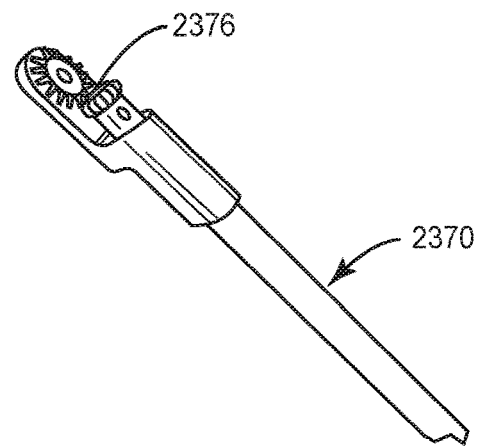
FIG. 23B is a perspective view of a head of a fastener applicator tool for affixing the helical-shaped coil fastener of FIG. 23A.

FIG. 23B is a perspective view of a head of a fastener applicator tool 2370 for affixing the helical-shaped coil fastener 2314 of FIG. 23A. The fastener applicator tool 2370 includes a 90 degree driver 2376 to hold and rotate the helical-shaped coil fastener 2314. The 90 degree driver 2376 press releases the helical-shaped coil fastener 2314 when desired, and could snap back on to remove the helical-shaped coil fastener 2314 (e.g., reverse drive). Once installed, the haptic foot section 2224 of FIG. 22B could be pushed through the loop of the rectangular-shaped wire loop head 2334 to affix an IOL 2312 relative to the iris 104.

Figure 24A:
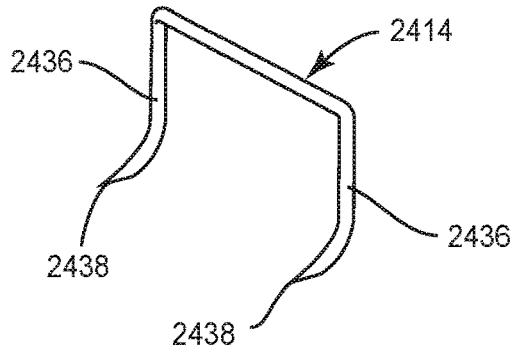
FIG. 24A is a perspective view of a staple fastener.
Figure 24B:
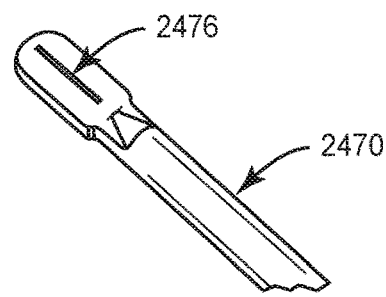
FIG. 24B is a perspective view of a fastener applicator tool for affixing the staple fastener of FIG. 24A.

FIG. 24A is a perspective view of a staple fastener 2414 to be used with the fastener applicator tool 2470 shown in FIG. 24B. An IOL assembly includes all of the components discussed with respect to FIGS. 2A-3E and FIG. 22B above, including an enlarged haptic foot section 2224, except for the inclusion of a staple fastener 2414. The staple fastener 2414 includes a first and second pointed tip 2438, the first and second pointed tips 2438 extending in the same direction, and angled relative to first and second arms 2436 of the staple fastener 2414. In this way, the staple fastener 2414 can be rotatingly inserted into the iris tissue. In other words, the staple fastener 2414 enters the iris 104 at an angle. A haptic can then be inserted and secured similar to FIG. 22B. In other words, the staple fastener 2414 (e.g., clip), can then capture the haptic of the implant to the iris 104.

FIG. 24B is a perspective view of a fastener applicator tool 2470 for affixing the staple fastener 2414 of FIG. 24A. The fastener applicator tool 2470 includes a slit 2476 at an end thereof to receive a portion of the staple fastener 2414.

Figure 25A:
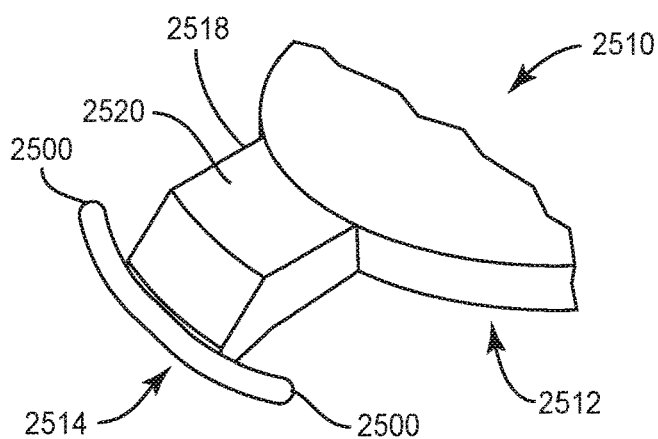
FIG. 25A is a perspective view of an IOL assembly with a spring wing fastener.
Figure 25B:
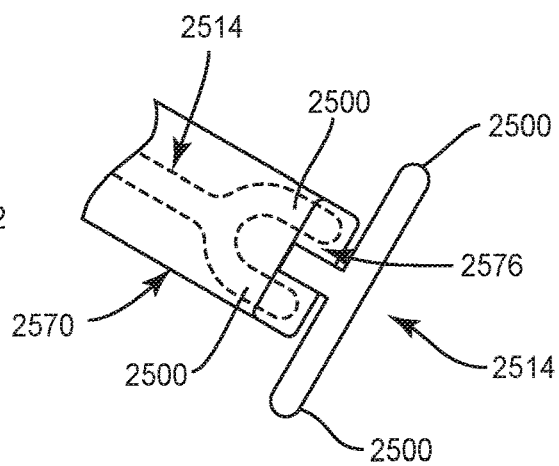
FIG. 25B is a perspective view of a fastener applicator tool for affixing the spring wing fastener of the IOL assembly of FIG. 25A within the iris.

FIGS. 25A and 25B are views of an IOL assembly 2510 with a spring wing fastener 2514. The IOL assembly 2510 of FIG. 25A includes all of the components discussed with respect to FIGS. 2A-3E above, except that a haptic 2518 includes a spring wing fastener 2514 at a distal end thereof (and/or at a distal end of a riser section 2520 of the haptic 2518). The spring wing fastener 2514 could be curved and include first and second ends 2500 that extend past ends of the haptic 2518. The spring wing fastener 2514 could include a blade on a bottom surface thereof to cut into the iris 104 and/or the spring wing fastener 2514 could be inserted into pre-made cuts in the iris 104 (with the wings folded). Once in the cut, the spring wing fastener 2514 could open, thereby holding an IOL 2512 in place.

FIG. 25B is a perspective view of a fastener applicator tool 2570 for affixing the spring wing fastener 2514 of the IOL assembly of FIG. 25A to the iris 104. The fastener applicator tool 2570 is a sleeve defining a channel 2576. The width of the channel 2576 is less than the width of the spring wing fastener 2514, such that when the fastener applicator tool 2570 is slipped on, the first and second ends 2500 flex forward (as shown in dotted lines), and when the fastener applicator tool 2570 is slipped off, the first and second ends 2500 flex towards their natural (e.g., straight or curved) orientation (as show in solid lines).

Embodiments disclosed herein are exemplary, and may be provided together in any combination desired. Those skilled in the art will recognize improvements and modifications to the embodiments disclosed herein. Many modifications and other embodiments of the invention set forth herein will come to mind to one skilled in the art to which the invention pertains having benefit of the teachings presented in the foregoing descriptions and the associated drawings. All such improvements and modifications are considered within the scope of the concepts disclosed herein.

It is also noted that the operational steps described in any of the exemplary embodiments herein are described to provide examples and discussion. The operations described may be performed in numerous different sequences other than the illustrated sequences. Furthermore, operations described in a single operational step may actually be performed in a number of different steps. Additionally, one or more operational steps discussed in the exemplary embodiments may be combined. It is to be understood that the operational steps illustrated in the flow chart diagrams may be subject to numerous different modifications as will be readily apparent to one of skill in the art.

Further, it is to be understood that the embodiments are not limited to the specific embodiments disclosed and that modifications and other embodiments are intended to be included within the scope of the appended claims. It is intended that the embodiments cover the modifications and variations of this invention provided they come within the scope of the appended claims and their equivalents. Although specific terms are employed herein, they are used in a generic and descriptive sense only and not for purposes of limitation.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but is to be accorded the widest scope consistent with the principles and novel features disclosed herein.

What is claimed is:

1. An intraocular lens assembly configured to be inserted and affixed in an eye with a crystalline lens, comprising:
   an intraocular lens comprising an optic for producing a preselected optical effect, the optic comprising an outer peripheral edge;
   a haptic extending from the outer peripheral edge of the optic, the haptic comprising a proximal end, a distal end, and a riser section therebetween, the proximal end at the outer peripheral edge of the optic at a different height than the distal end;
   a helical-shaped coil fastener comprising a wire comprising an end portion with a pointed tip, the wire forming a helix with a helical pitch defining a central cylindrical aperture, the helical-shaped coil fastener configured to affix the haptic to the eye by insertion through the distal end of the haptic and rotatable penetration into an anterior side of an iris; and a grommet positioned in the distal end of the haptic, the grommet comprising internal threads;

wherein the helical-shaped coil fastener is pre-loaded in the grommet; and wherein the internal threads of the grommet are configured to mate with the helical-shaped coil fastener to guide translation of the helical-shaped coil fastener relative to the grommet.

2. The intraocular lens assembly of claim 1, wherein the intraocular lens further comprises the haptic.

3. The intraocular lens assembly of claim 1, wherein the intraocular lens is configured to fit through an incision smaller than 4 mm in length.

4. The intraocular lens assembly of claim 1, configured to attach to the iris and avoid interfering with sphincter and dilator muscles of the iris.

5. The intraocular lens assembly of claim 1, wherein the helical-shaped coil fastener is configured to penetrate the iris to a depth so as not to penetrate pigment epithelium.

6. The intraocular lens assembly of claim 1, wherein the preselected optical effect comprises an effect comprised from the group consisting of myopia, hyperopia, astigmatism, or combinations thereof.

7. The intraocular lens assembly of claim 1, wherein the preselected optical effect comprises a first optical effect comprised from the group consisting of myopia, hyperopia, astigmatism, or combinations thereof, and incorporates a second optical effect to correct for presbyopia.

8. The intraocular lens assembly of claim 7, wherein the optic is configured to work in conjunction with a natural crystalline lens of the eye.

9. The intraocular lens assembly of claim 7, wherein the optic is configured to work without a natural crystalline lens of the eye.

10. The intraocular lens assembly of claim 1, wherein the optic comprises an optical feature comprised from the group consisting of a refractive feature, a defractive feature, a multifocal feature, a bifocal feature, extended range of focus or vision feature, and an aspherized feature.

11. The intraocular lens assembly of claim 1, wherein:
the haptic comprises a plurality of haptics; and
the helical-shaped coil fastener comprises a plurality of helical-shaped coil fasteners,
each of the plurality of haptics affixed to the iris by one of the plurality of helical-shaped coil fasteners.

12. The intraocular lens assembly of claim 1, wherein the distal end comprises a cavity configured to receive the helical-shaped coil fastener therein.

13. The intraocular lens assembly of claim 1, wherein the distal end comprises a bottom wall, the helical-shaped coil fastener configured to be inserted through the bottom wall to affix the haptic to the eye.

14. The intraocular lens assembly of claim 1, wherein the proximal end of the haptic comprises a plurality of proximal ends connected to the outer peripheral edge of the optic.

15. The intraocular lens assembly of claim 1, wherein the haptic is integrally connected to the optic.

16. The intraocular lens assembly of claim 1, wherein the helical-shaped coil fastener is configured to rotatably penetrate into the anterior side of the iris when rotated in a first direction and to rotatably remove from the anterior side of the iris when rotated in a second direction, the second direction opposite the first direction.

17. The intraocular lens assembly of claim 1, wherein a top portion of the helical-shaped coil fastener includes a head, a head width being wider than a helical diameter of the wire.

18. The intraocular lens assembly of claim 1, wherein a top portion of the helical-shaped coil fastener includes a head, a head width being approximately the same size as a helical diameter of the wire.

19. The intraocular lens assembly of claim 1, wherein the intraocular lens assembly is configured so that the helical-shaped coil fastener is recessed relative to a top surface of the haptic when the helical-shaped coil fastener is fully penetrated into the iris to affix the haptic to the eye.

20. The intraocular lens assembly of claim 1, wherein the helical-shaped coil fastener further comprises a groove along a length of the wire of the helical-shaped coil fastener.

* * * * *